United States Patent
Nakano et al.

(10) Patent No.: US 8,634,069 B2
(45) Date of Patent: Jan. 21, 2014

(54) DEFECT INSPECTION DEVICE AND DEFECT INSPECTION METHOD

(75) Inventors: Hiroyuki Nakano, Mito (JP); Shunji Maeda, Yokohama (JP); Toshihiko Nakata, Hiratsuka (JP)

(73) Assignee: Hitachi High-Technologies Corporation, Tokyo (JP)

(*) Notice: Subject to any disclaimer, the term of this patent is extended or adjusted under 35 U.S.C. 154(b) by 319 days.

(21) Appl. No.: 12/992,903

(22) PCT Filed: May 13, 2009

(86) PCT No.: PCT/JP2009/002083
§ 371 (c)(1),
(2), (4) Date: Feb. 14, 2011

(87) PCT Pub. No.: WO2009/139155
PCT Pub. Date: Nov. 19, 2009

(65) Prior Publication Data
US 2011/0149275 A1    Jun. 23, 2011

(30) Foreign Application Priority Data

May 16, 2008 (JP) ................................ 2008-129314

(51) Int. Cl.
*G01N 21/88* (2006.01)
(52) U.S. Cl.
USPC ...................................... 356/237.1; 356/237.3
(58) Field of Classification Search
USPC ..................................... 356/237.1–237.5, 369
See application file for complete search history.

(56) References Cited

U.S. PATENT DOCUMENTS

| 5,046,847 A * | 9/1991 | Nakata et al. ................. 356/338 |
| 6,195,202 B1 | 2/2001 | Kusunose |
| 6,411,377 B1 * | 6/2002 | Noguchi et al. ........... 356/237.4 |
| 2005/0213086 A1 * | 9/2005 | Hamamatsu et al. ...... 356/237.2 |
| 2007/0070337 A1 | 3/2007 | Ohshima et al. |
| 2008/0068593 A1 | 3/2008 | Nakano et al. |
| 2008/0204724 A1 | 8/2008 | Hamamatsu et al. |
| 2009/0141264 A1 | 6/2009 | Shibata et al. |
| 2010/0088042 A1 | 4/2010 | Noguchi et al. |
| 2010/0265496 A1 | 10/2010 | Nakano et al. |
| 2011/0149275 A1 * | 6/2011 | Nakano et al. ............. 356/237.2 |
| 2011/0255074 A1 * | 10/2011 | Nakano et al. ................. 356/51 |

FOREIGN PATENT DOCUMENTS

| JP | 10-090192 | 4/1998 |
| JP | 10-282010 | 10/1998 |
| JP | 2000-105203 | 4/2000 |
| JP | 2000-155099 | 6/2000 |

(Continued)

*Primary Examiner* — Hoa Pham
(74) *Attorney, Agent, or Firm* — Antonelli, Terry, Stout & Kraus, LLP.

(57) ABSTRACT

A defect inspection device, which inspects defects such as foreign materials existing on a specimen on which a circuit pattern of wiring or the like is formed, is provided with an illumination optical system which illuminates a plurality of different areas the specimen with a plurality of linear shaped beams and an image forming optical system that forms images of the plurality of the illuminated areas on a plurality of detectors, and the detectors are configured to receive a plurality of polarization components substantially at the same time and individually, wherein the polarization components are different from each other and are contained in each of the plurality of the optical images formed by the image forming optical system, thereby detecting a plurality of signals corresponding to the polarization components and carrying out the inspection at high speed under a plurality of optical conditions.

15 Claims, 41 Drawing Sheets

(56) References Cited

FOREIGN PATENT DOCUMENTS

| JP | 2003-017536 | 1/2003 |
|----|-------------|--------|
| JP | 2005-024327 | 1/2005 |
| JP | 2005-214966 | 8/2005 |
| JP | 2005-283190 | 10/2005 |
| JP | 2007-85958 | 4/2007 |
| JP | 2007-085958 | 4/2007 |
| JP | 2007-192759 | 8/2007 |
| JP | 2008-096430 | 4/2008 |

* cited by examiner

FIG. 12A
FIG. 12B
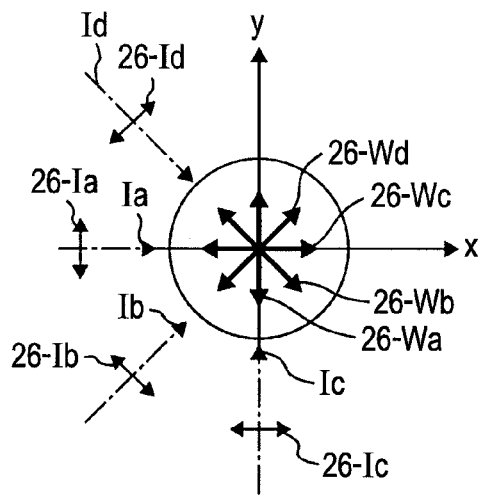
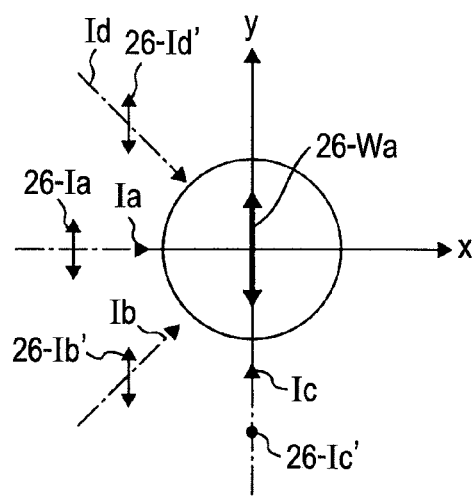
FIG. 13
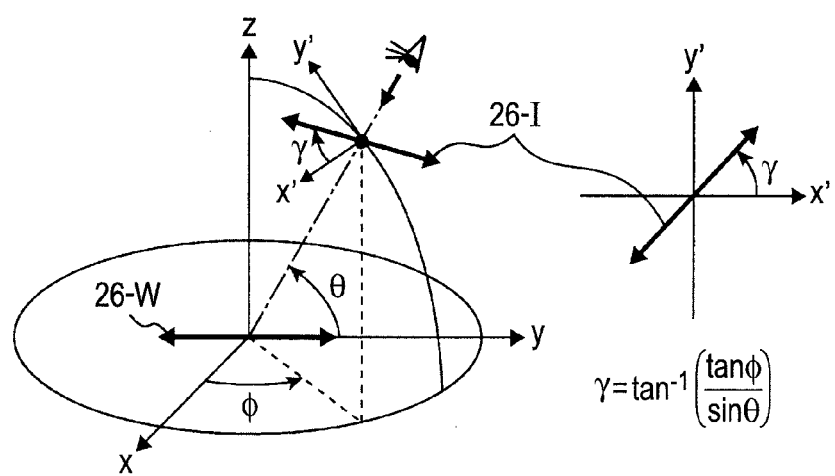
$$\gamma = \tan^{-1}\left(\frac{\tan\phi}{\sin\theta}\right)$$

FIG. 15A
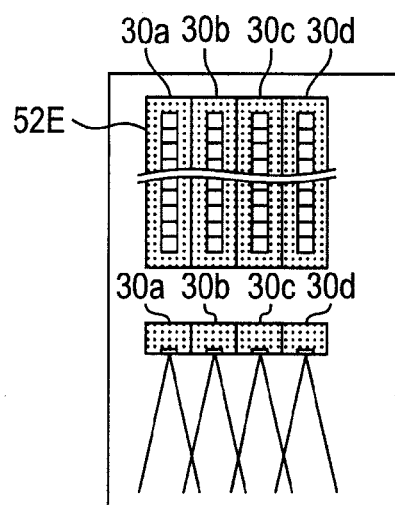
FIG. 15B
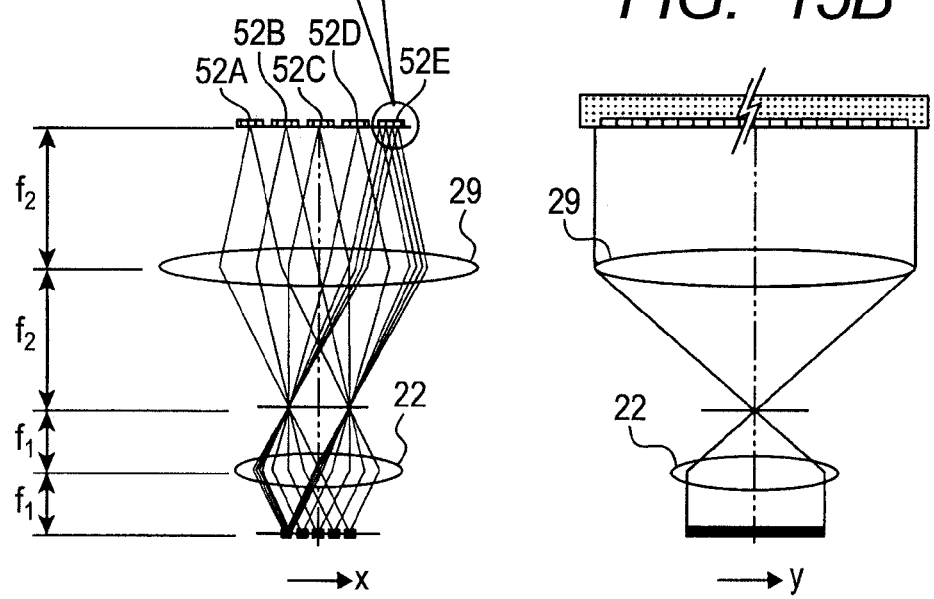
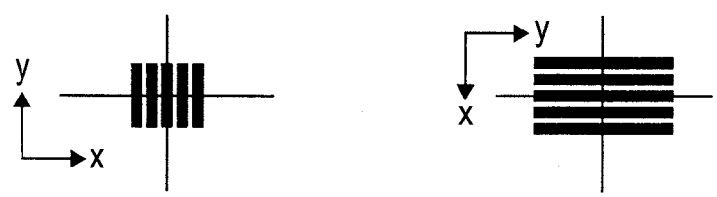

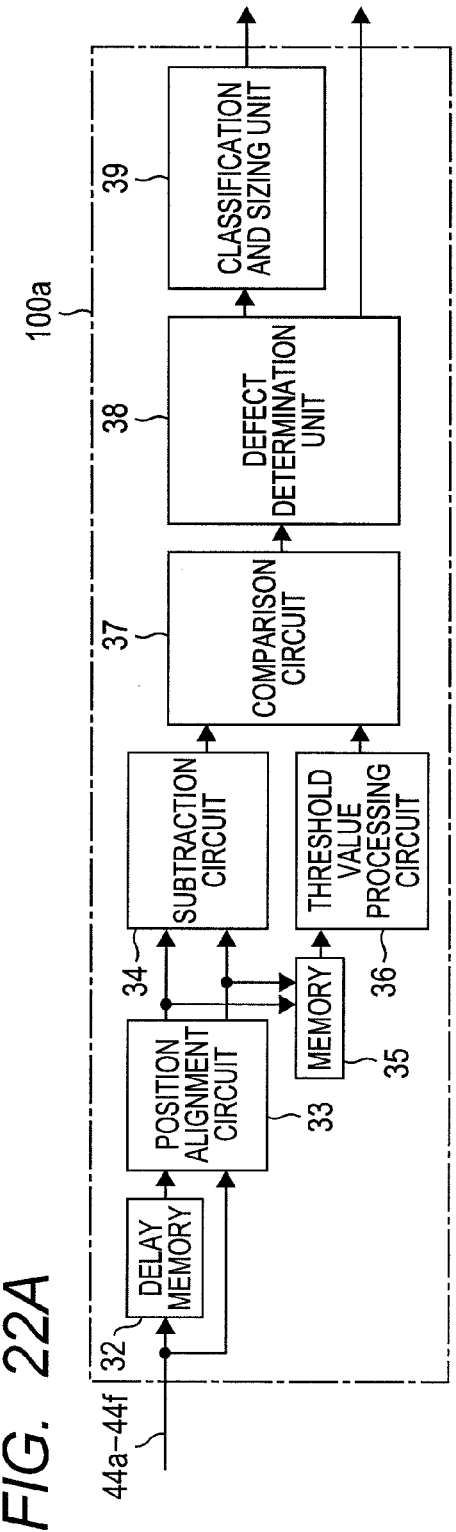
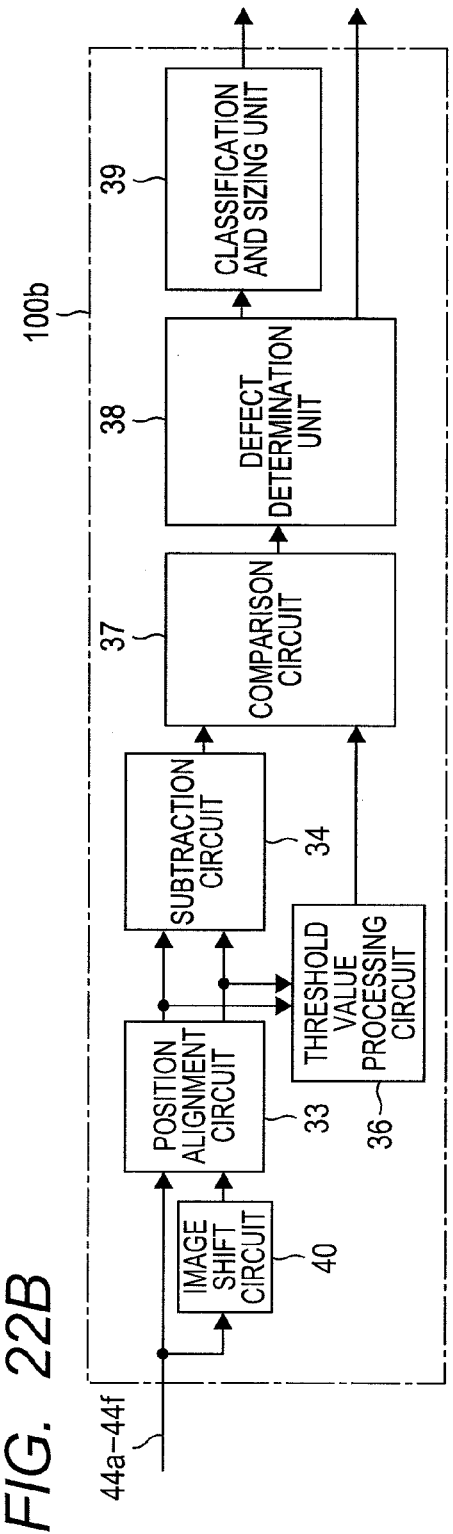
FIG. 22A
FIG. 22B

DEFECT INSPECTION DEVICE AND DEFECT INSPECTION METHOD

BACKGROUND

The present invention relates to a defect inspection device and a defect inspection method capable of inspecting defects such as foreign materials generated on an object to be inspected at the time of manufacturing an LSI or a liquid crystal substrate, etc.

When an LSI or a liquid crystal substrate, etc., are manufactured, as a pattern formed on an object to be processed (for example, a semiconductor wafer), there are a repetitive pattern as represented by a dynamic random access memory (DRAM) part or a random pattern (non-repetitive pattern) represented by logic. In manufacturing the LSI or liquid crystal substrate, etc., when foreign materials are attached to a surface of an object to be processed or defects are generated, it serves as factors causing, for example, an insulation defect, short-circuit, etc., of a wiring. In this case, as a circuit pattern is increasingly fined, there may be a need to discriminate a pattern (non-defective part) formed on the object to be processed and various kinds of fine foreign materials or defects (wiring short, disconnection, pattern thinning, pattern thickening, scratch, non-hole opening, or the like).

However, in order to discriminate the pattern (non-defective part) and various kinds of fine foreign materials or defects, there is a need to change optical conditions including a plurality of illuminating conditions or detecting conditions.

By the way, as the related art of the defect inspection device, JP-A-Hei10(1998)-90192 (Patent Document 1), JP-A-2000-105203 (Patent Document 2), JP-A-2000-155099 (Patent Document 3), JP-A-2003-17536 (Patent Document 4), JP-A-2005-283190 (Patent Document 5), and JP-A-2007-192759 (Patent Document 6) have been known.

In other words, Patent Document 1 discloses an optical inspection device for a sample including a dark-field illumination system and a bright-field illumination system alternately irradiating the same point of a first pattern, a dark-field image detector detecting a reflected image of the first pattern in a dark field, and a bright-field image detector detecting a reflected image of the first pattern in a bright field.

Further, Patent Document 2 discloses a defect inspection device including an illumination optical system for illuminating a slit-type beam to a substrate to be inspected from a plurality of different azimuth directions by switching a light path and a detecting optical system receiving reflected, scattered light provided from defects such as foreign materials, existing on the lighted substrate to be inspected by using an image sensor, converting it into a signal, and detecting the signal.

Further, Patent Document 3 discloses a high-resolution device for observation of a sample surface including an illumination optical system performing polarization lighting on a sample, a polarization optical component more efficiently transmitting polarization-rotated higher-order diffracted light in a sample than zero-order light, and a detecting optical system imaging an image of the sample on a photoelectric transformation device by light transmitting the polarization optical component or reflected therefrom.

Further, Patent Document 4 discloses a pattern inspection device including a floodlight optical system irradiating laser light having wavelength different from each other on a surface of an object to be inspected at different incident angles, a condenser optical system shielding reflected light from the surface of the object to be inspected using a spatial filter and receiving scattered light transmitting the spatial filter, a second dichroic mirror that splits the scattered light condensed in the condenser optical system into different wavelengths, two CCD cameras each receiving and imaging the scattered light that are wavelength-split in the second dichroic mirror, and an image processing unit processing the imaging output of the CCD cameras to determine whether there are defects.

Further, Patent Document 5 discloses defect inspection device including an illumination optical system having a plurality of irradiation units irradiating illuminated light flux emitted from a lighting light source to a surface of a sample from a plurality of azimuth directions different from each other and a light path switching unit switching the illuminated light flux, a vertical direction detecting optical system receiving an optical image scattered in a normal direction among reflected, scattered light from the surface of the sample and converting it into an image signal, an oblique direction detecting optical system receiving an optical image scattered in an oblique direction among reflected, scattered light from the surface of the sample and converting it into an image signal, and an image signal processing unit processing the image signal obtained from both detecting optical systems to detect defects.

In addition, Cited Reference 6 discloses a defect detection device including an irradiation optical system irradiating first and second slit-type beams to a substrate to be inspected from both sides at an inclined angle from the predetermined inclined direction on a plane, a detecting optical system condensing reflected, scattered light from defects existing on the irradiated substrate to be inspected and converting and detecting the condensed reflected, scattered light into a light receiving signal by an image sensor, and an image processing unit extracting a signal indicating defect based on the detected signal, as shown in FIG. 5

DOCUMENTS OF PRIOR ART

Patent Documents

[Patent Document 1] JP-A-Hei10(1998)-90192
[Patent Document 2] JP-A-2000-105203
[Patent Document 3] JP-A-2000-155099
[Patent Document 4] JP-A-2003-17536
[Patent Document 5] JP-A-2005-283190
[Patent Document 6] JP-A-2007-192759

DISCLOSURE OF THE INVENTION

Problem To Be Solved By The Invention

However, in Patent Document 1, the optical conditions for detecting defects such as foreign materials are very limited to the dark field and the bright field.

Further, in Patent Documents 2, 5, and 6, the lighting conditions that are the optical conditions for detecting various kinds of foreign materials or defects are basically changed for various kinds of foreign materials or defects. This requires long detection time for one sample and greatly degrades the throughput.

Further, in Patent Document 3, the optical conditions for detecting defects such as foreign materials are very limited to the polarization lighting and the polarization detection.

In addition, in Patent Document 4, the deice irradiates different laser light having wavelengths different from each other to the surface of the object to be inspected at different incident angles, splits the scattered light on the surface of the object to be inspected into different wavelengths, and receives and images the wavelength-split scattered light in each of the CCD cameras. The optical conditions for detecting defects such as foreign materials are very limited.

The present invention is to provide a defect inspection device and a defect inspection method capable of inspecting defects such as foreign materials generated on various patterns formed on the object to be processed without degrading the throughput even when the inspection is needed under a plurality of optical conditions, in order to inspect the defects by discriminating them from a normal circuit pattern, during the manufacturing of the LSI or the liquid crystal substrate.

Means for Solving the Problems

According to an embodiment of the present invention, there are provided a defect inspection apparatus and a defect inspection method, including: an illumination optical system which illuminates a specimen to be inspected with a linear shaped beam; an imaging optical system which images a reflected, scattered light image generated from defects existing on the substrate to be inspected by the illumination of the linear shaped beam from the illumination optical system; a spatial filter disposed in the imaging optical system so as to shield diffracted light generated from a repetitive pattern formed on the specimen; a detector which receives a light image obtained through the spatial filter and imaged in the imaging optical system to detect signals; a defect determining unit which processes the signals detected in the detector to determine defects; and a classification and sizing processing unit which classifies defects determined in the defect determining unit and calculates a size of the defect, wherein the detector receives a plurality of polarization components different from each other included in the light image imaged in the imaging optical system at almost the same time or individually to detect the signals as a plurality of signals corresponding to the plurality of polarization components.

Further, according to another embodiment of the present invention, there are provided a defect inspection apparatus and a defect inspection method, including: an illumination optical system which illuminates plural positions on a specimen to be inspected with a plurality of linear shaped beams at almost the same time; an imaging optical system imaging a plurality of reflected, scattered light images generated from defects existing on the substrate to be inspected by illuminating the plurality of positions with the plurality of linear shaped beams emitted from the illumination optical system; a spatial filter disposed in the imaging optical system so as to shield diffracted light generated from a repetitive pattern formed on the substrate to be inspected; a detector which receives a plurality of light images obtained through the spatial filter and imaged in the imaging optical system at almost the same time or individually to detect a plurality of signals; a defect determining unit which processes the plurality of signals detected in the detector to determine defects due to foreign materials, etc.; and a classification and sizing processing unit which classifies defects determined in the defect determining unit and classifies a size of the defect.

Further, according to another embodiment of the present invention, there are provided a defect inspection apparatus and a defect inspection method, including: an illumination optical system which illuminates a plurality of irradiation positions (inspection regions) on a specimen to be inspected which are different from each other with a plurality of linear shaped beams at almost the same time; an imaging optical system which images a plurality of reflected, scattered light images generated from defects existing on the substrate to be inspected by illuminating the plurality of positions on the specimen with the plurality of linear shaped beams emitted from the illumination optical system; a spatial filter disposed in the imaging optical system so as to shield diffracted light generated from a repetitive pattern formed on the substrate to be inspected; a detector detecting receiving a plurality of light images obtained through the spatial filter and imaged in the imaging optical system at almost the same time or individually to detect a plurality of signals; a defect determining unit processing the plurality signals detected in the detector to determine defects; and a classification and sizing processing unit classifying defects determined in the defect determining unit and calculating a size of the defect, wherein the detector receives a plurality of polarization components different from each other included in each of the plurality of light images imaged in the imaging optical system at almost the same time or individually to detect each of the plurality of signals as a plurality of signals corresponding to the plurality of polarization components.

Further, according to another embodiment of the present invention, there are provided a defect inspection apparatus and a defect inspection method, including: an illumination optical system which illuminates a specimen to be inspected with a linear shaped beam; an imaging optical system imaging a reflected light image generated from the substrate to be inspected by the illumination of the linear beam emitted from the illumination optical system; a spatial filter disposed in the imaging optical system so as to shield diffracted light generated from a repetitive pattern formed on the substrate to be inspected; a detector which receives a light image obtained through the spatial filter and imaged in the imaging optical system to detect signals; a defect determining unit which processes the signals detected in the detector to determine defects due to foreign materials, etc.; and a classification and sizing processing unit which classifies defects determined in the defect determining unit and classifies a size of the defect, wherein the detector is configured of a CMOS type image sensor that can be processed in a pixel unit.

Further, the present invention individually captures the diffracted and scattered light by illuminating the plurality of linear shaped beams during one-time scanning and collectively processes the plurality of captured images to extract the signals based on the defects existing on the substrate to be inspected. Further, the present invention classifies the extracted signals for each defect kind or calculates the information of the size of the defect.

According to the embodiments of the present invention, it is possible to perform the inspection at high sensitivity without degrading the throughput due to the image capturing, defect decision, classification, and sizing during one-time scanning under the plurality of optical conditions.

BRIEF DESCRIPTION OF THE DRAWINGS

FIG. 12A is a diagram for explaining polarization of illuminated light of each azimuth and a vibration direction of electric field on a semiconductor wafer W, wherein all the polarization states 26-Ia to 26-Id of illuminated light Ia to Id are S polarization and the state where vibration directions 26-Wa to 26-Wd of electric field on the semiconductor wafer W do not match each other is shown, and FIG. 12B shows a case where ones projected onto the surface of the semiconductor wafer W are set to be parallel with a y-axis and the vibration direction of electric field on the surface of the semiconductor wafer W is set to be parallel with a y-axis by being matched with 26-Wa, to show the polarization states 26-Ia and 26-Ib' to 26-Id' of illumination Ia to Id of each azimuth angle φ;

FIG. 13 is a diagram for explaining conditions for making the polarization of illuminated light on the sample into the linearly polarized light parallel with a y-axis in the illumination optical system according to Embodiment 1 of the present invention;

FIG. 15A is a front view showing in detail the detecting optical system according to Embodiment 1 of the present invention and FIG. 15B is a side view of the detecting optical system;

FIG. 22A is a diagram showing a configuration, where die comparison processing as signal processing conditions is executed, in the signal processing unit according to Embodiment 1 of the present invention, FIG. 22B is a diagram showing a configuration, where cell comparison processing as signal processing conditions is executed, in the signal processing unit according to Embodiment 1 of the present invention.

BEST MODES FOR CARRYING OUT THE INVENTION

Embodiments of a defect inspection method and a defect inspection device according to the present invention will be described with reference to the accompanying drawings.

Embodiment 1

Embodiment 1 of a defect inspection method and a defect inspection device according to the present invention will be described.

Figure 1A:
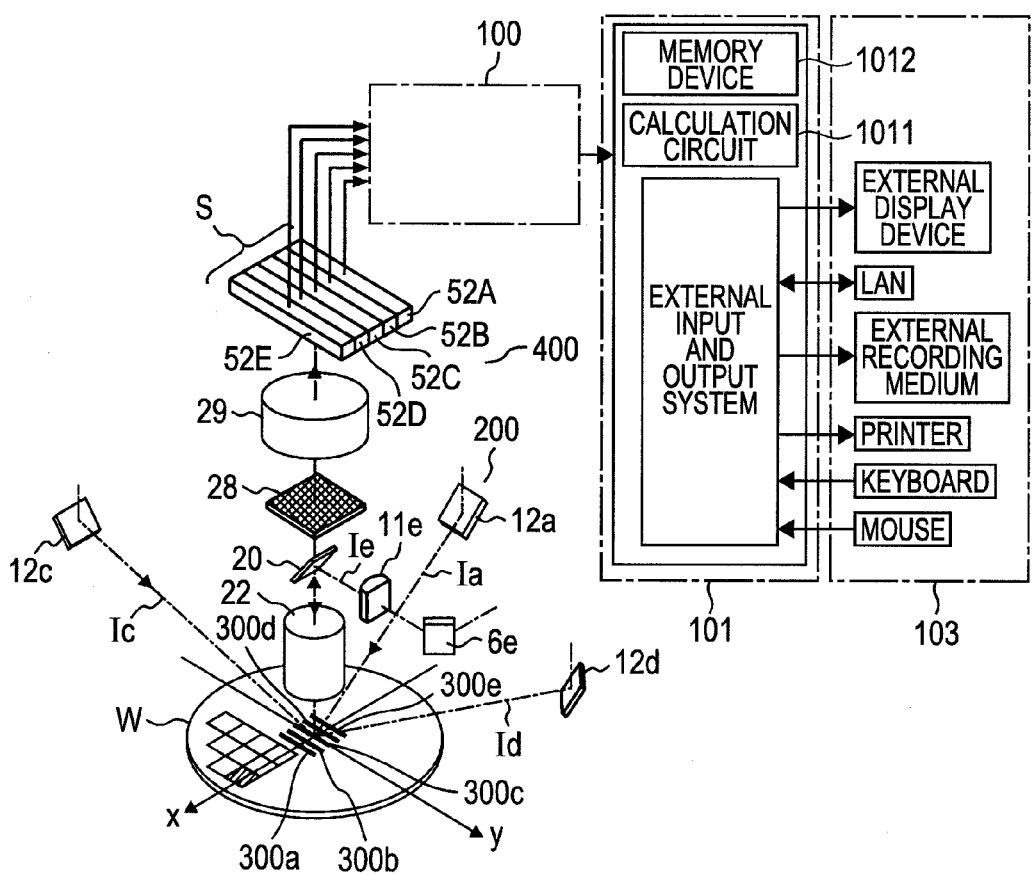
FIG. 1A is a perspective view showing a schematic configuration of a defect inspection device according to Embodiment 1 of the present invention and FIG. 1B is a diagram showing pixels of a linear sensor array projected on a semiconductor wafer.
Figure 1B:
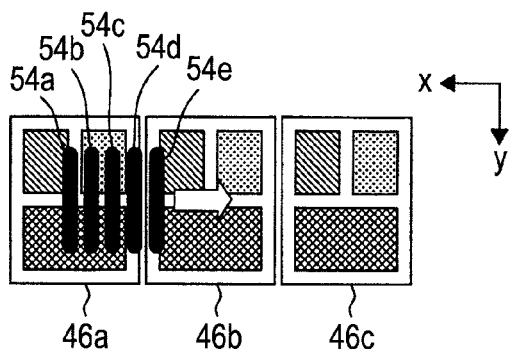

FIG. 1 is a perspective view showing a schematic configuration of a defect inspection device according to Embodiment 1 of the present invention. An illumination optical system 200 is configured so that for example, five linear shaped beams (straight line-like beam) 300a, 300b, 300c, 300d, and 300e having different illuminating conditions (for example, including an illuminating azimuth angle φ, an Incidence elevation angle θ, a polarization state of illuminating light, and an illuminating beam intensity) are illuminated on a sample (semiconductor wafer) W in parallel. Each of linear beams 300a to 300d are illuminated by the reflection from each mirror 12a to 12d for adjusting an incidence angle and the linear beam 300e is illuminated through an objective lens 22 from the top side. A detecting optical system 400 is configured to include an objective lens 22, a spatial filter 28 disposed on a Fourier transformation plane, an imaging lens 29 imaging, for example, each of the five linear beams 300a to 300e onto each of the five linear sensor arrays 52A to 52E configured in lines, and a detector S configured by arranging in lines, for example, five linear sensor arrays 52A to 52E. Further, each of 54a to 54e represents a pixel of each of the linear sensor array projected onto the wafer W. In addition, each of 46a to 46c represents dies formed on the wafer W. Therefore, light scattered and diffracted to a normal direction of the semiconductor wafer generated from foreign materials, defects, and patterns on the semiconductor wafer by the illumination of each of linear beams 300a, 300b, 300c, 300d, and 300e from, for example, is condensed by the objective lens 22. When the pattern formed on the semiconductor wafer W has a repetitive shape, since the diffracted light generated from the repetitive pattern is condensed at a regular interval on an exit pupil of an objective lens 22, that is, a Fourier transformation plane, the diffracted light is shielded by the spatial filter 28 disposed on the Fourier transformation plane. The scattered light generated from other than the repetitive pattern by the illumination of each of linear beams 300a, 300b, 300c, 300d, and 300e, that is, the scattered and diffracted light generated from the foreign materials, defects, and patterns on the semiconductor wafer W is guided into the imaging lens 29 through the spatial filter 28 and imaged on, for example, each of the five linear sensor arrays 52A, 52B, 52C, 52D, and 52E. In addition, reference numeral 23 represents an X stage, reference numeral 24 represents a Y stage, and reference numeral 25 represents a rotation stage.

Figure 2:
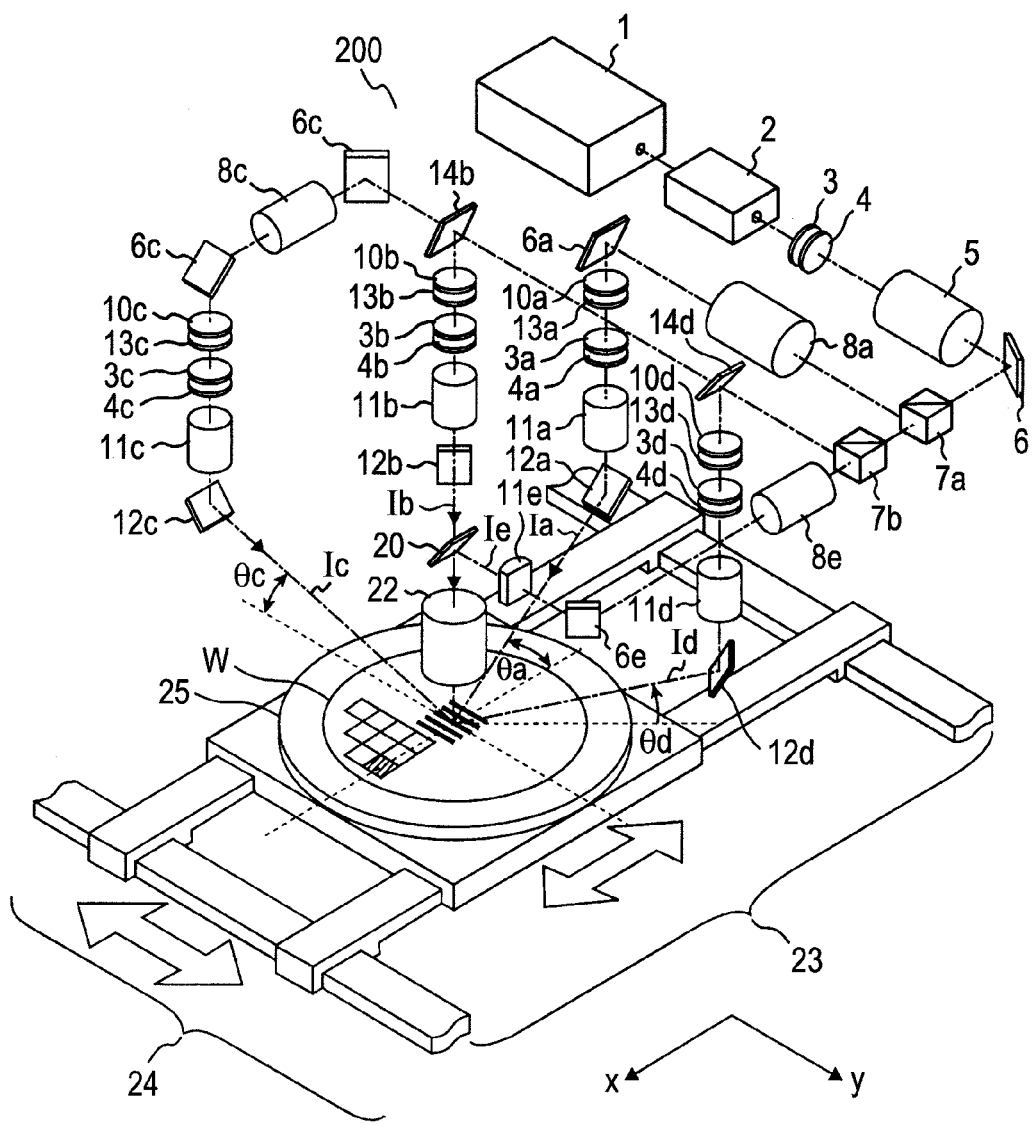
FIG. 2 is a perspective view showing other configurations other than a detecting optical system in Embodiment 1 of the present invention.
Figure 3:
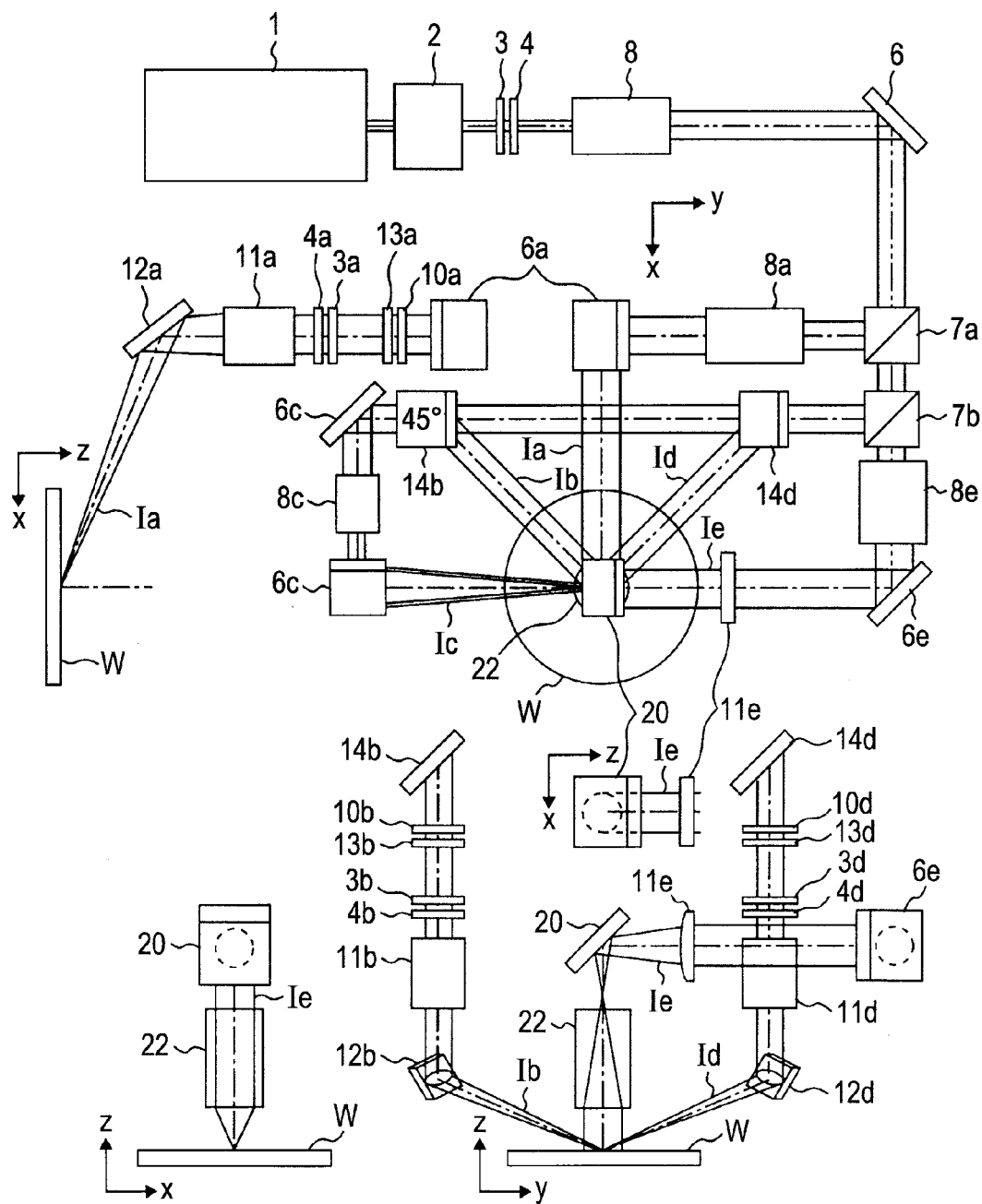
FIG. 3 is a diagram showing an illumination optical system in Embodiment 1 of the present invention.

Next, Embodiment 1 of the illumination optical system 200 will be described in detail with reference to FIGS. 2 to 13. In other words, as shown in FIGS. 2 and 3, an output of a linearly polarized beam oscillated from a laser light source 1 is controlled by an attenuator 2 and is guided into a ½ wavelength plate 3 and a ¼ wavelength plate 4. Further, light paths of each illuminating orientation is configured to include ½ wavelength plates 3a to 3d and ¼ wavelength plates 4a to 4d.

In this configuration, functions implemented by the ½ wavelength plates 3, 3a to 3d and ¼ wavelength plates 4, 4a to 4d will be described with reference to FIG. 4. In other words, any polarization states that are illuminating conditions can be implemented by the ½ wavelength plates 3, 3a to 3d and the ¼ wavelength plates 4, 4a to 4d as shown FIGS. 4A to 4D.

Figure 4A:
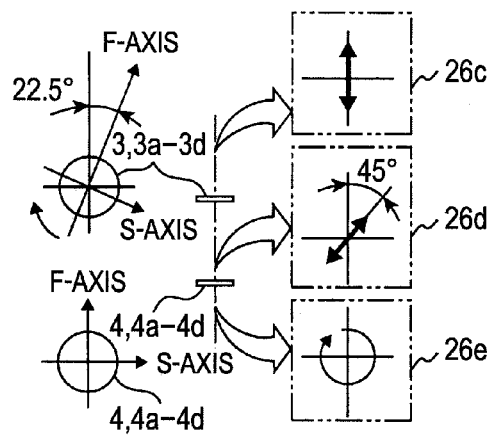
FIG. 4A is a diagram for explaining a mechanism adjusting polarization of illuminated light in the illumination optical system according to Embodiment 1 of the present invention and conditions creating circularly polarized light and linearly polarized light in any direction and shows conditions creating circularly polarized light.

FIG. 4A shows conditions creating circularly polarized light. In other words, when linearly polarized light 26c is incident into the ½ wavelength plate 3, if the optical axis of each of the ½ wavelength plates 3, 3a to 3d is inclined 22.5°, emitted light becomes 45° inclined linearly polarized light 26d. The optical axis of the ¼ wavelength plate 4 is set to allow the 45° inclined linearly polarized light 26d to be incident at an angle of 45° with respect to the optical axis of the ¼ wavelength plate 4, such that the emitted light becomes circularly polarized light 26e.

Figure 4B:
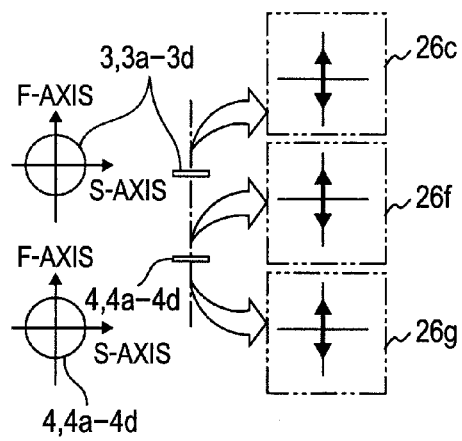
FIG. 4B is a diagram for explaining a mechanism adjusting polarization of illuminated light in the illumination optical system according to Embodiment 1 of the present invention and conditions creating circularly polarized light and linearly polarized light in any direction and shows conditions not changing the polarization state of incident light.

FIG. 4B shows conditions where the polarization state 26c of incident light is not changed. That is, when the linearly polarized light 26c is incident into each of the ½ wavelength plates 3, 3a to 3d, if the optical axes of each of the ½ wavelength plates 3, 3a to 3d are not inclined (0°), polarization 26f of the emitted light of each of the ½ wavelength plates 3, 3a to 3d is not changed from 26c. Further, if the optical axes of each of the ¼ wavelength plates 4, 4a to 4d are not also inclined) (0°), polarization 26g of the emitted light of each of the ¼ wavelength plates 4, 4a to 4d is not changed from 26c.

Figure 4C:
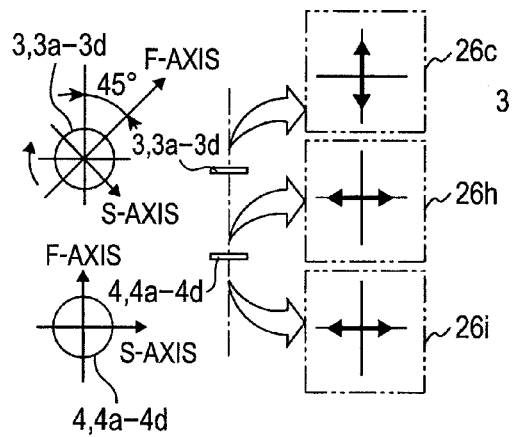
FIG. 4C is a diagram for explaining a mechanism adjusting polarization of illuminated light in the illumination optical system according to Embodiment 1 of the present invention and conditions creating circularly polarized light and linearly polarized light in any direction and shows conditions under which the polarization state of incident light rotates 90°.

FIG. 4C shows conditions where the polarization state 26c of incident light rotates 90°. That is, when the linearly polarized light 26c is incident into each of the ½ wavelength plates 3, 3a to 3d, if the optical axes of each of the ½ wavelength plates 3, 3a to 3d are inclined 45°, polarization 26h of the emitted light of each of the ½ wavelength plates 3, 3a to 3d is inclined 90° with respect to 26c. Thereafter, if the optical axes of each of the ¼ wavelength plates 4, 4a to 4d are not also inclined) (0°), polarization 26i of the emitted light of each of the ¼ wavelength plates 4, 4a to 4d is also inclined 90° with respect to 26c.

Figure 4D:
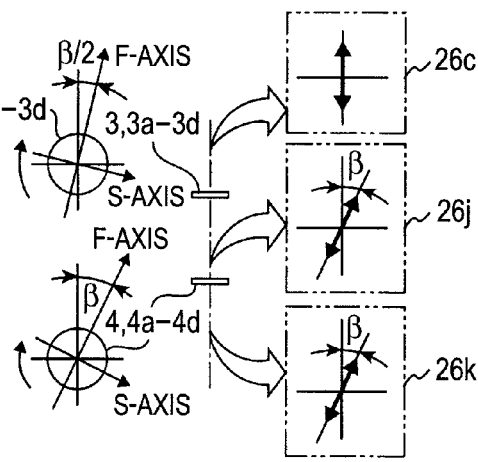
FIG. 4D is a diagram for explaining a mechanism adjusting polarization of illuminated light in the illumination optical system according to Embodiment 1 of the present invention and conditions creating circularly polarized light and linearly polarized light in any direction and shows conditions creating linearly polarized light inclined by any angle β.

FIG. 4D shows conditions of creating the linearly polarized light inclined by any angle β. That is, when the linearly polarized light is finally inclined by β, the optical axes of each of the ½ wavelength plates 3, 3a to 3d is first inclined by β/2. Thereby, polarization 26j of the emitted light of each of the ½ wavelength plates 3, 3a to 3d is inclined by β with respect to the linearly polarized light 26c. Thereafter, if the optical axes of each of the ¼ wavelength plates 4, 4a to 4d are also inclined by β, polarization 26k of the emitted light of each of the ¼ wavelength plates 4, 4a to 4d becomes linearly polarized light inclined by β with respect to 26c.

As shown in FIGS. 2 and 3, light from the ¼ wavelength plate 4 is expanded in a beam expander 8 (beam diameter becomes w) in order to obtain a desired beam width on the semiconductor wafer W. The beam output from the beam expander is reflected by a mirror 6, and branched into two light paths by a beam splitter 7a. The reflected light at the beam splitter 7a is expanded 1.4 times (root two times) by the beam expander 8a to be matched with a longitudinal linear beam size (length) from each azimuth angle on the semiconductor waver W (beam diameter: 1.4w). The expanded beam is reflected to the lower side by the mirror 6a, wherein the polarization state is adjusted by two linear polarizing plates 10a and 13a that are disposed in series and the ½ wavelength plate 3a and the ¼ wavelength plate 4a that are also disposed in series. The polarization state adjusted beam is condensed at an off-axis by a cylindrical lens 11a, and an incident elevation angle θa is adjusted by the mirror 12a for adjusting an incidence angle to illuminate the linear beam 300a on the semiconductor wafer W in a desired elevation angle at an azimuth angle φ=0° (0° illuminating). Further, the transmission light at the beam splitter 7a is also branched into two light paths by another beam splitter 7b. The reflected light at the beam splitter 7b is also branched into two light paths by a branch optical element 14d such as a half mirror. The reflected light at the branch optical element 14d is reflected to a lower side, wherein the polarization state is adjusted by two linear polarizing plates 10d and 13d that are disposed in series and the ½ wavelength plate 3d and the ¼ wavelength plate 4d that are also disposed in series, similar to 0° illuminating. The light passed through the ¼ wavelength plate 4d is condensed at an off-axis by the cylindrical lens 11d, and the incident elevation angle θd is adjusted by the mirror 12d for adjusting an incidence angle to illuminate the linear beam 300d on the semiconductor wafer W in a desired elevation angle at the azimuth angle φ=−45°. In the case of −45° illuminating (azimuth angle φ is −45°), since an original beam diameter is w but the illuminating orientation (azimuth angle φ) is inclined 45°, the length of the linear beam 300d on the semiconductor wafer W becomes 1.4w, similar to 0° illuminating. The transmission light at the branch optical element 14d is branched into two light paths by a branch optical element 14b such as the half mirror. The reflected light at the branch optical element 14b is reflected to a lower side, wherein the polarization state is controlled by two linear polarizing plates 10b and 13b that are disposed in series and the ½ wavelength plate 3b and the ¼ wavelength plate 4b that are also disposed in series, similar to the 0° illuminating. The light passed through the ¼ wavelength plate 4b is condensed at an off-axis by the cylindrical lens 11b, and the incident elevation angle θb is adjusted by the mirror 12b for adjusting an incidence angle to illuminate the linear beam 300b on the semiconductor wafer W in a desired elevation angle at the azimuth angle φ=45°. In the case of the 45° lighting, since an original beam diameter is w but the illuminating orientation is inclined 45°, the length of the linear beam 300b on the semiconductor wafer W becomes 1.4w, similar to the 0° illuminating. The transmission light at the branch optical element 14b is reflected by the mirror 6c to go into the beam expander 8c, wherein the beam diameter is adjusted so that the longitudinal direction of the linear beam formed on the semiconductor wafer W becomes 1.4w by the beam expander 8c (the length of the linear beam formed on the semiconductor wafer W is changed by the incident elevation angle, such that the beam diameter is adjusted according to the incident elevation angle). The light passed through the beam expander 8c is then reflected to a lower side by the mirror 6c, wherein the polarization state is adjusted by two linear polarizing plates 10c and 13c that are disposed in series and the ½ wavelength plate 3c and the ¼ wavelength plate 4c that are also disposed in series, and condensed at an off-axis by a cylindrical lens 11c, similar to the 0° illuminating. The incident elevation angle θc is adjusted by the mirror 12c for adjusting an incidence angle to illuminate the linear beam 300c on the semiconductor wafer W in a desired elevation angle at the azimuth angle φ=90°. The transmission light at the beam splitter 7b is expanded 1.4 times (root two times) by the beam expander 8e to be matched with a longitudinal linear beam size (length) of lights incident from each azimuth angle on the semiconductor waver W (beam diameter: 1.4w). The light passed through the beam expander 8e is reflected at the mirror 6e, condensed at an off-axis by the cylindrical lens 11e, and reflected to a lower side by the half mirror 20, and the linear beam 300e is illuminated on the semiconductor wafer W from a direction parallel with a normal direction of the semiconductor wafer W through the objective lens 22. As described above, the illuminating of the linear beam 300e becomes the epi-illumination. Further, the intensity of epi-illumination is adjusted by the attenuator 2 and the polarization direction (polarization state) of the epi-illumination is adjusted by the ½ wavelength plate 3 and the ¼ wavelength plate 4.

Figure 5:
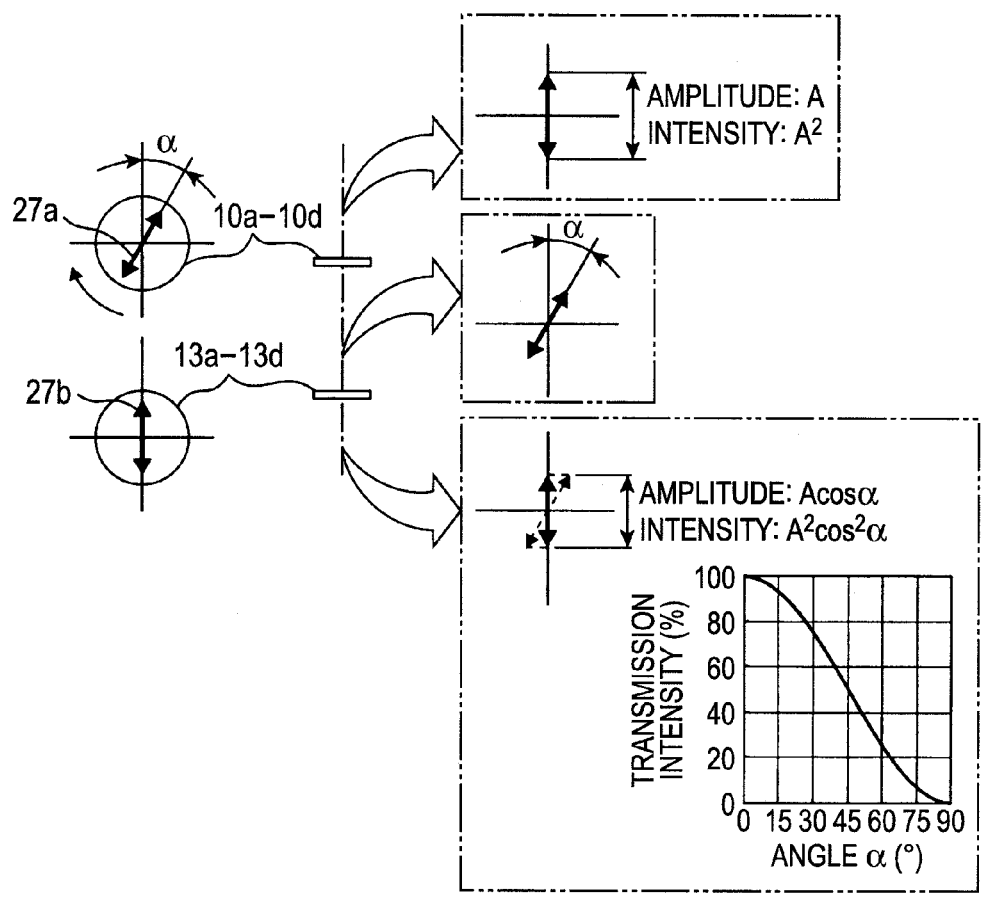
FIG. 5 is a diagram for explaining a mechanism adjusting illuminated light quantity of each branched light path in the illumination optical system according to Embodiment 1 of the present invention.

Further, the operation of the linear polarizing plates 10a to 10d and 13a to 13d that are disposed in series will be described with reference to FIG. 5. For example, the light incident into each of the linear polarizing plate 10a to 10d becomes linear polarization (slope is 0°) of amplitude A (intensity $A^2$). In this case, when the transmission axis of each of the linear polarizing plate 13a to 13d becomes 0°, if each of the linear polarizing plate 10a to 10d rotates by α, the intensity of light emitted from each of the linear polarizing plate 13a to 13d becomes $(A \cdot \cos \alpha)^2$. Thus, the intensity of beam that is an illuminating condition irradiated on the semiconductor waver W may be optionally adjusted.

Each of the polarization state of lights passed through each of the linear polarizing plates 13a to 13d is adjusted by the ½ wavelength plate 3a to 3d and the ¼ wavelength plates 4a to 4d that are each disposed in series (the operation is the same as one described in the ½ wavelength plate 3 and the ¼ wavelength plate 4). Each of the lights passed through each of the ¼ wavelength plates 4a to 4d is condensed at an off-axis by each of the cylindrical lenses 11a to 11d, and the incident elevation angle is adjusted by each of the mirrors 12a to 12d for adjusting an incidence angle to form each of linear beams 300a to 300d separated from each other on the semiconductor wafer W in a line at a desired elevation angle. Further, in Embodiment 1, the longitudinal direction of each of linear beams 300a to 300e formed in a line to be separated from each other on the semiconductor wafer W becomes a y-axis, as shown in FIG. 1.

Figure 6:
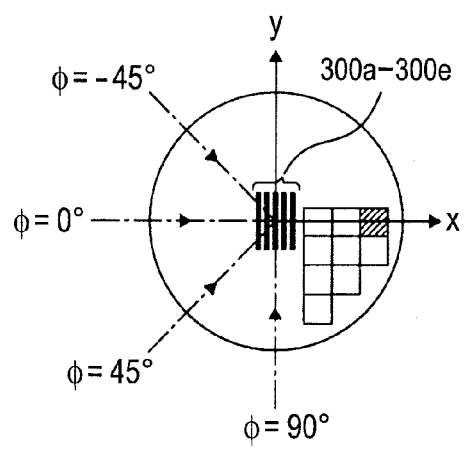
FIG. 6 is a diagram showing definition of an illuminating azimuth angle in the illumination optical system according to Embodiment 1 of the present invention

Next, the definition of the illuminating azimuth angle φ at which, for example, five linear beams 300a to 300e are irradiated on the semiconductor wafer W in a line will be described with reference to FIG. 6. In Embodiment 1, the illuminating of the linear beam 300a from a negative direction on an x-axis by the mirror 12a for adjusting an incidence angle is defined as φ=0°, the illumination of the linear beam 300c from a negative direction on a y-axis by the mirror 12c for adjusting an incidence angle is defined as φ=90°, the illumination of the linear beam 300b from between 0° and 90° is defined as φ=45°, and the illumination of the linear beam 300d from an angle symmetrical with 45° with respect to an x-axis is defined as φ=−45°. In addition, the length of the linear beam on the semiconductor wafer W of the 0° illumination becomes 1.4w.

Figure 7:
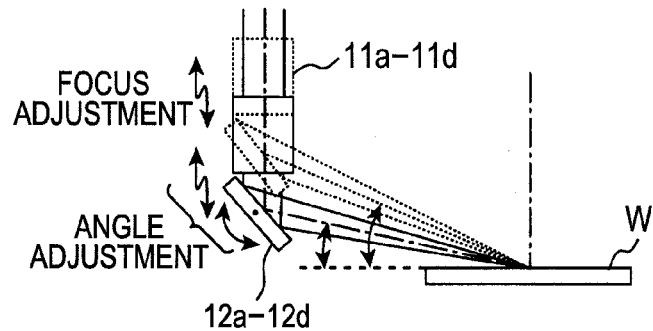
FIG. 7 is a diagram showing a mechanism adjusting an incident elevation angle in the illumination optical system according to Embodiment 1 of the present invention.
Figure 8:
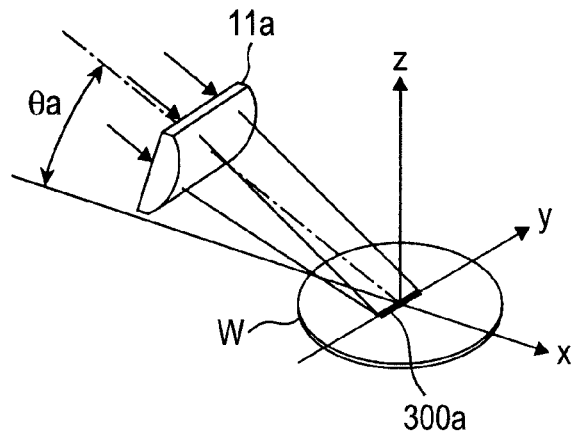
FIG. 8 is a diagram showing a method for forming condensed linear spot beam in a transverse direction and parallel in a longitudinal direction, which is a y direction, on the sample from the azimuth angle 0° in the illumination optical system according to Embodiment 1 of the present invention.

Further, the incident elevation angles θa to θd of each of linear beams 300a to 300d is adjusted by changing the height and angle of the mirrors 12a to 12d for adjusting an incidence angle, as shown in FIG. 7. Further, since the distance to the surface of semiconductor wafer W is changed according to each incident elevation angle, the cylindrical lenses 11a to 11d simultaneously move in the optical axis direction to adjust a focus so that the illuminated beam is condensed on the surface of the semiconductor wafer W. FIG. 8 shows a configuration where parallel light is formed in the longitudinal direction on the semiconductor wafer W, that is, a y-axis direction from a direction (incident elevation angle direction θa) inclined by θa with respect to a horizontal plane by the cylindrical lens 11a and the condensed linear beam 300a is formed in an x-axis direction, in the case where the illuminating azimuth angle is φ=0°. In addition, the reflection of beam by the mirror 12a for adjusting an incidence angle is not shown. In this case, the ridge line of the spherical surface of the cylindrical lens 11a may be parallel with a y-axis and a plane of the cylindrical lens 11a may be disposed to be vertical with respect to the main light beam.

Figure 9:
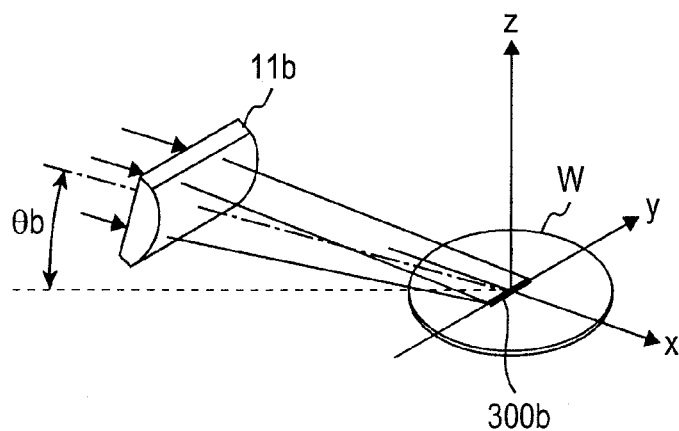
FIG. 9 is a diagram showing a method for forming condensed linear spot beam in a transverse direction and parallel in a longitudinal direction, which is a y direction, on the sample from the azimuth angle 45° in the illumination optical system according to Embodiment 1 of the present invention.

FIG. 9 shows a configuration where parallel light is formed in the longitudinal direction on the semiconductor wafer W, that is, a y-axis direction from a direction (incident elevation angle direction θb) inclined by θb with respect to a horizontal plane by the cylindrical lens 11a and the condensed linear beam 300b is formed in an x-axis direction, in the case where the illuminating azimuth angle is φ=45°. In addition, the reflection of beam by the mirror 12b for adjusting an incidence angle is not shown. In this case, the ridge line of the spherical surface of the cylindrical lens 11b may be parallel with a y-axis direction and a plane of the cylindrical lens 11b may be disposed to be inclined by 45° with respect to the main optical axis.

Figure 10:
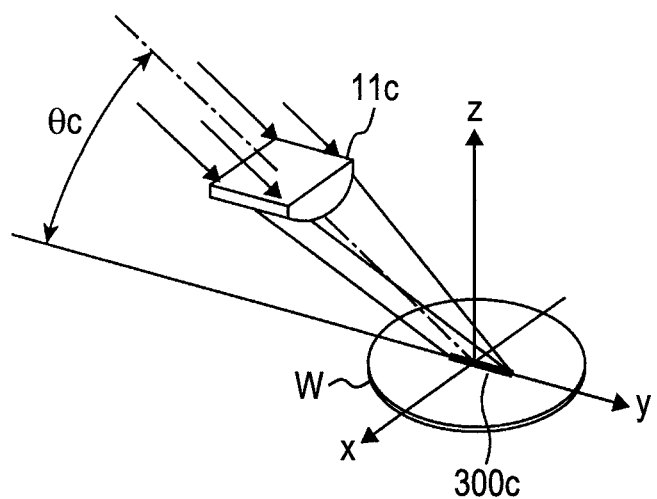
FIG. 10 is a diagram showing a method for forming condensed linear spot beam in a transverse direction and parallel in a longitudinal direction, which is a y direction, on the sample from the azimuth angle 90° in the illumination optical system according to Embodiment 1 of the present invention.

FIG. 10 shows a configuration where parallel light is formed in the longitudinal direction on the semiconductor wafer W, that is, a y-axis direction from a direction (incident elevation angle direction θc) inclined by θc with respect to a horizontal plane by the cylindrical lens 11c and the condensed linear beam 300c is formed in an x-axis direction, in the case where the illuminating azimuth angle is φ=90°. In addition, the reflection of beam by the mirror 12c for adjusting an incidence angle is not shown. In this case, the ridge line of the spherical surface of the cylindrical lens 11c may be parallel with a y-axis direction and a plane of the cylindrical lens 11c may be disposed to be inclined by the same θc as the incident elevation angle with respect to the main optical axis.

Figure 11:
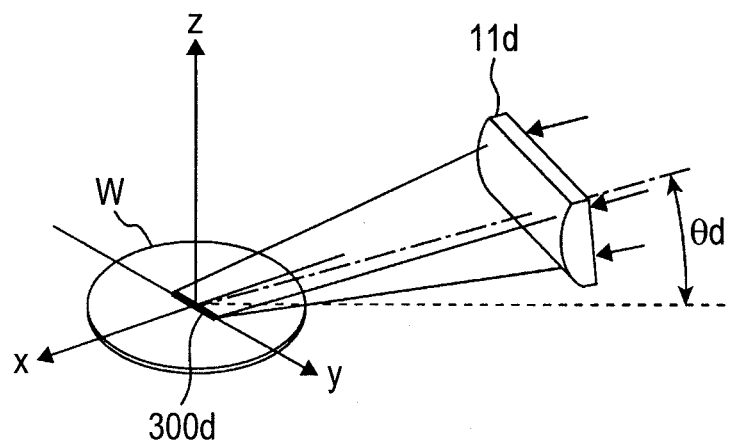
FIG. 11 is a diagram showing a method for forming condensed linear spot beam in a transverse direction and parallel in a longitudinal direction, which is a y direction, on the sample from the azimuth angle −45° in the illumination optical system according to Embodiment 1 of the present invention.

FIG. 11 shows a configuration where parallel light is formed in the longitudinal direction on the semiconductor wafer W, that is, a y-axis direction from a direction (incident elevation angle direction θd) inclined by θd with respect to a horizontal plane by the cylindrical lens 11d and the condensed linear beam 300d is formed in an x-axis direction, in the case where the incidence azimuth angle is φ=−45°. In addition, the reflection of beam by the mirror 12d for adjusting an incidence angle is not shown. In this case, the ridge line of the spherical surface of the cylindrical lens 11d may be parallel with a y-axis direction and a plane of the cylindrical lens 11d may be disposed to be inclined by 45° with respect to the main optical axis.

Next, the polarization of the illuminated light of each azimuth angle and the vibration direction of electric field on the semiconductor wafer W will be described with reference to FIGS. 12A and 12B. In FIG. 12A, all the polarization states 26-Ia to 26-Id of the illuminated light Ia to Id are S polarization. In this case, the vibration directions 26-Wa to 26-Wd of electric field on the semiconductor wafer W do not match with each other. As shown in FIG. 12B, when wishing to match the vibration direction of electric field on the surface of the semiconductor wafer W with, for example, 26-Wa and is parallel with a y-axis, there is a need to study the polarization state of the illumination Ia to Id of each azimuth angle φ. That is, the state where the polarization state of the illumination Ia to Id of each azimuth angle φ is projected to the surface of the semiconductor wafer W as shown in 26-Ia, 26-Ib' to 26-Id' should not be parallel with a y-axis. However, the polarization direction to be set by the incident elevation angles θa to θd is substantially changed. FIG. 13 shows a preferable polarization angle of the illumination light Ia to Id in the case of setting the vibration direction of electric field on the semiconductor wafer W in parallel with a y-axis. In this case, a plane vertical to a propagation direction of the illumination light Ia to Id is an x'-y' plane and liner polarization may be inclined by γ with respect to an x'-axis, wherein γ, which is a function of the illuminating azimuth angle φ and the incident elevation angle θ, depends on the following Equation 1.n $$\gamma = \tan^{-1}(\tan\phi/\sin\theta) \qquad (1)$$

This may be obtained by simple coordinate transformation and may be calculated each time according to the vibration direction 26-W of electric field to be set on the semiconductor wafer W to determine the polarization state 26-1 of the illumination Ia to Id of each azimuth angle φ and to adjust the polarization state by the ½ wavelength plates 3a to 3d and the ¼ wavelength plates 4a to 4d that are disposed in series.

Figure 14A:
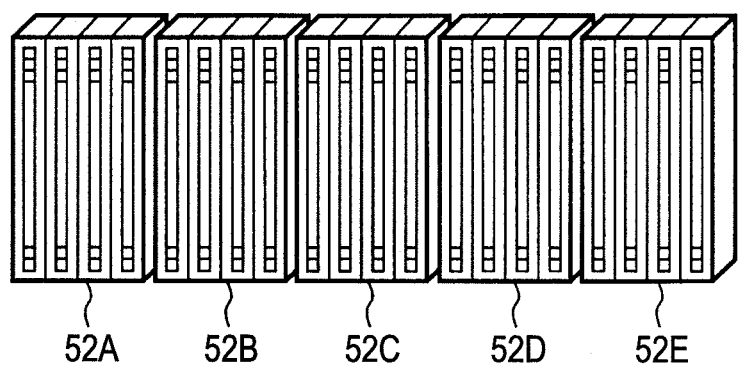
FIG. 14A is a perspective view showing a linear sensor array as a detector in a detecting optical system according to Embodiment 1 of the present invention and FIG. 14B is a diagram showing an illuminating area on the sample and pixels projected onto the sample.
Figure 14B:
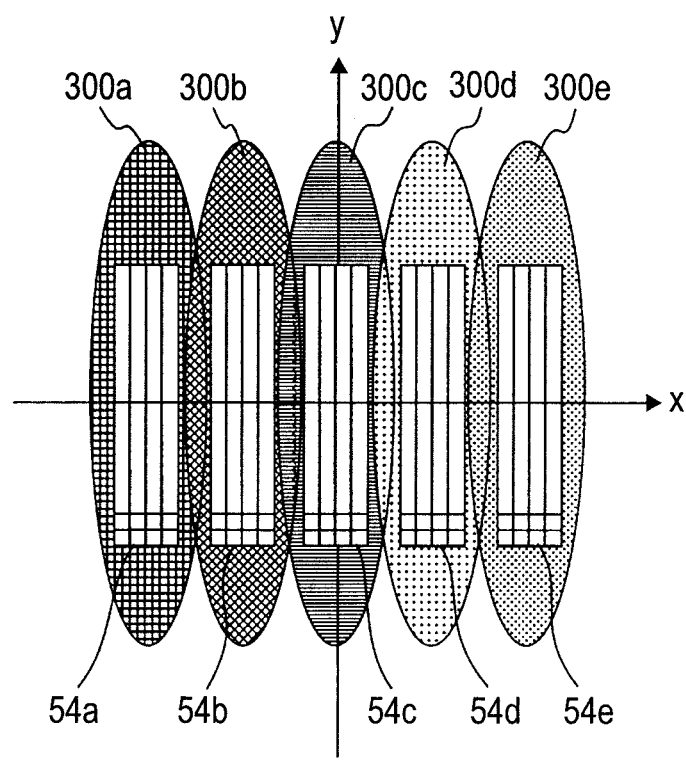

Next, the detecting optical system 400 according to Embodiment 1 will be described with reference to FIGS. 14A to 29. That is, the detecting optical system 400 according to Embodiment 1 is configured by arranging in lines, for example, five linear sensor arrays 52A to 52E in an x direction (scanning direction) as a detector S, as shown in FIG. 14A. Further, as shown in FIG. 14B, if detection magnification is set so that each of the pixels 54a to 54e of the linear sensor array projected on the semiconductor wafer W is in the range of the spot size of each of linear beams 300a to 300e, each of the pixels 54a to 54e of the linear sensor array can collectively detect the diffused and scattered light generated from the linear region, as shown in FIG. 15.

The semiconductor wafer W is mounted on X and Y stages 23 and 24 and each pixel 54a to 54e of the linear sensor array obtains a two-dimensional image of the semiconductor wafer W by scanning the semiconductor wafer W in X and Y directions by the X and Y stages 23 and 24. In this case, the principal scanning direction is set as an X direction that is a direction vertical with respect to the longitudinal direction of the linear beam and the entire surface of the semiconductor wafer W can be inspected at high speed by performing a step movement in a Y direction by the length of the pixel 54 of the linear sensor array projected onto the semiconductor wafer W.

Figure 16A:
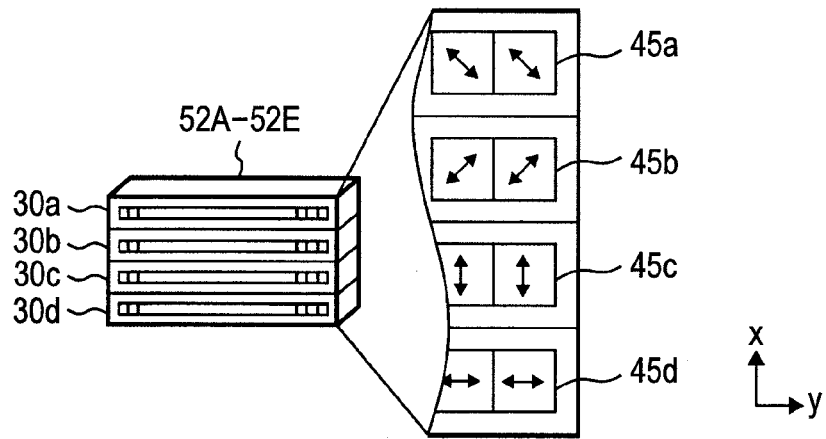
FIG. 16A is a perspective view showing a linear array sensor with polarizing elements for each pixel and four linear sensors with polarizing elements having different transmission axes as a detector in the detecting optical system according to Embodiment 1 of the present invention and FIG. 16B is a diagram showing an illuminating area on the sample and pixels projected onto the sample.
Figure 16B:
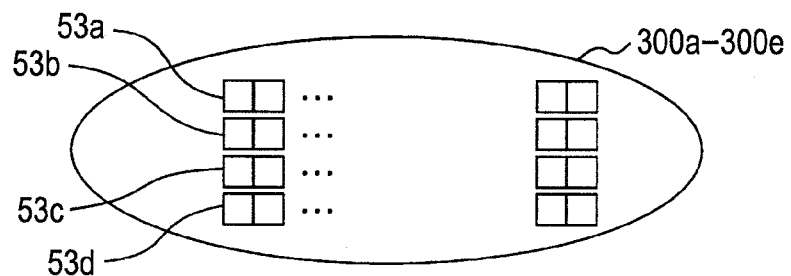
Figure 17:
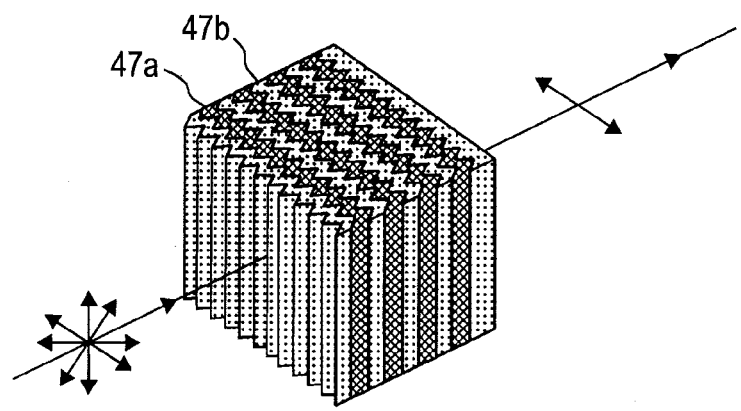
FIG. 17 is a diagram showing the polarizing elements using a photonic crystal included in four linear sensors as the detector in the detecting optical system according to Embodiment 1 of the present invention.
Figure 18A:
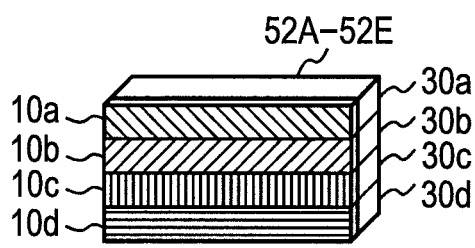
FIG. 18A is a diagram showing four linear sensors as the detector where linear polarizing plates each having different transmission axes in the detecting optical system according to Embodiment 1 of the present invention are disposed at a front surface and FIG. 18B is a diagram showing the transmission axes of each polarizing plate.

Hereinafter, each of the linear sensor arrays 52A to 52E corresponding to each of linear beams 300a to 300e will be described. By the way, each of the linear sensor arrays 52A to 52E is configured by arranging in lines, for example, one-dimensional four linear sensors 30a to 30d in an X direction (scanning direction), as shown in FIG. 16A. Herein, each of the one-dimensional four linear sensors 30a, 30b, 30c, and 30d is attached with pixels 45a, 45b, 45c, and 45d of a linear polarizing film having transmission axes different from each other. Therefore, as shown in FIG. 16B, if the detection magnification is set so that each of the pixels 53a to 53d of the four linear sensors corresponding to each of the linear sensor arrays 52A to 52E projected on the semiconductor wafer W is in the range of the spot size of each of linear beams 300a to 300e, a signal obtained by analyzing the diffused and scattered light generated from each of the linear regions at different polarization axes (analyzing axis) can be collectively, simultaneously, or individually detected. That is, the images obtained by four detection conditions (for example, polarization axes are different from each other (polarization component)) can be collectively, simultaneously, or individually separation-detection) by one-time scanning. Regarding the polarizing film, as shown in FIG. 17, the transmitting polarization axis may be changed by the way of superimposing the photonic crystals 47a and 47b or by the combination of the different kind of the crystals. Further, it is possible to create the polarizing film formed from the photonic crystal in a pixel unit. One advantage of using the photonic crystal film is that, while the conventional polarization element, which is made by polarizing in anisotropic by aligning molecules in one direction after absorbing iodine in a film, is susceptible particularly to wavelengths lower than UV, the photonic crystal film is highly resistant to wavelengths lower than UV and high-output light. When there is no risk of tolerance, lifespan, etc., each of the general linear polarizing plates 10a, 10b, 10c, and 10d may be disposed in front of the linear sensors 30a, 30b, 30c, and 30d, as shown in FIG. 18A. Of course, the linear polarizing plate including the photonic crystal may also be used.

The four linear sensors 30a, 30b, 30c, and 30d configuring each linear sensor 52A to 52E observe different positions on the semiconductor wafer W at the same time. That is, the positions of images of each linear sensor obtained at the same time are shifted from each other. In this case, for example, the linear sensor is the linear CCD "IT-P1-2048" manufactured by DALSA Corp. When the pixel size of IT-P1-2048 is 10 μm and the size of pixel projected onto the semiconductor wafer W is 2 μm, the detection magnification determined at a ratio of a focus distance between the objective lens 22 and the imaging lens 29 becomes 10 times. In this case, since the package size of IT-P1-2048 (transverse direction, including wiring pin part) is 12.7 mm, the pixel interval of the adjacent linear sensors on the semiconductor wafer W becomes 2.54 mm. Since a line rate becomes 46 kHz maximally, that is, 0.022 ms, the scanning rate becomes 9.1 mm/s. That is, the time required to move between the pixels of the adjacent linear sensor becomes 0.28 ms. In this case, since the image from each linear sensor is differently distorted due to the influence of vibration of stage, etc., when the image processing shown in FIGS. 22A to 22C to be described below is performed, there is a need to perform the alignment processing. However, for example, the linear sensors 30a to 30d corresponding to 4 lines can be manufactured on the same substrate to be adjacent to each other. When the linear sensor array is manufactured according to the above method, the pixel interval of the adjacent linear sensor on the semiconductor wafer W becomes, for example, 2 μm and 2 μm on the semiconductor wafer W, that is, since the distortion of the image during one pixel movement may be disregarded, there is no need to perform the alignment processing when the image processing shown in FIGS. 22A to 22(c) to be described below is performed.

Figure 18B:
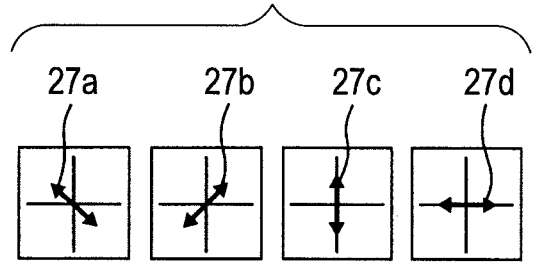
Figure 19:
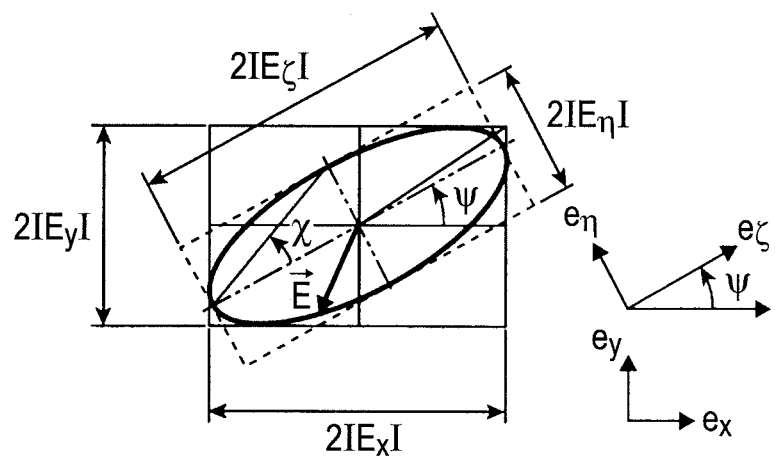
FIG. 19 is a diagram for explaining parameters showing the polarization states of an output from each linear sensor as the detector in the detecting optical system according to Embodiment 1 of the present invention.
Figure 20:
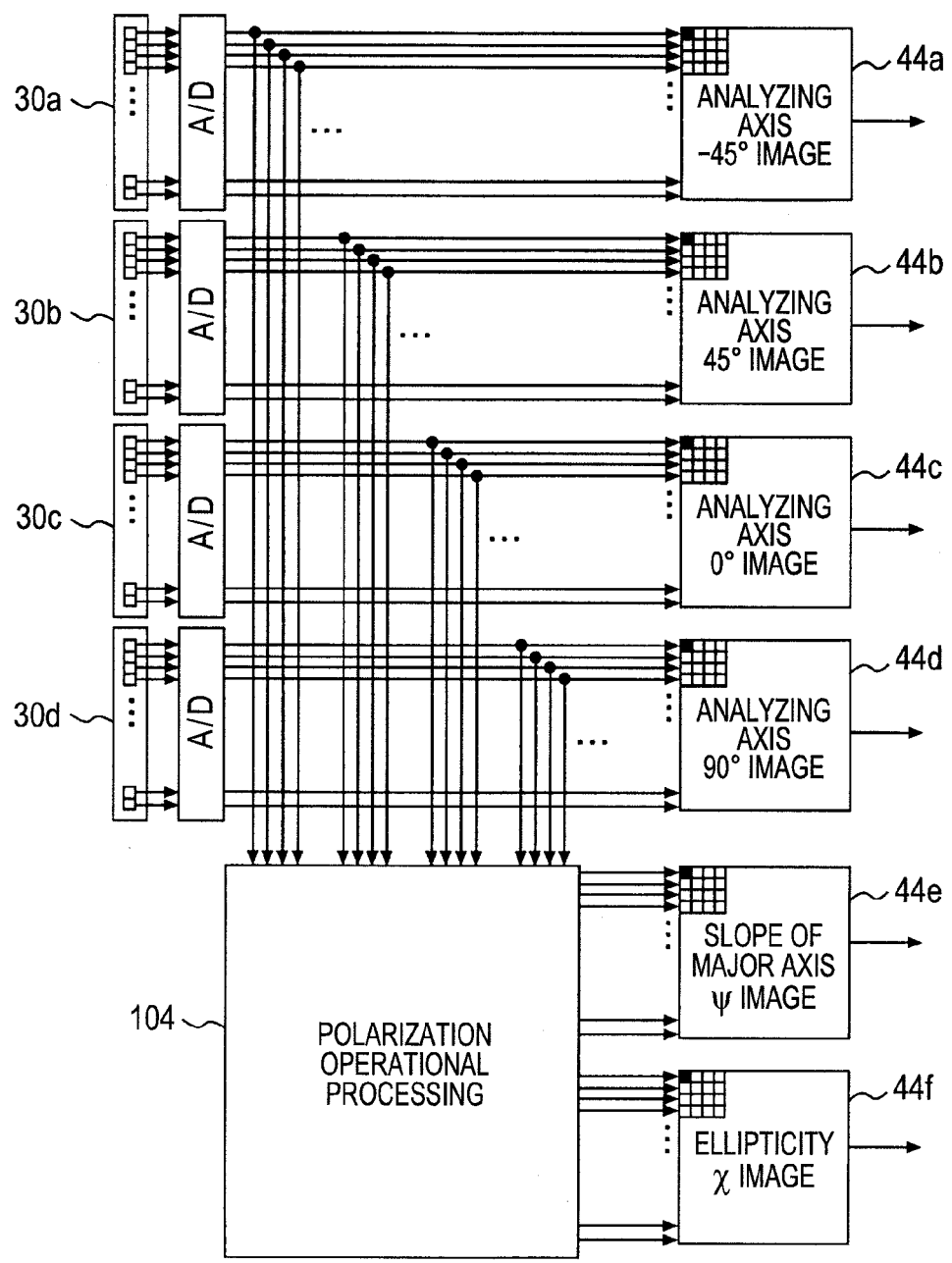
FIG. 20 is a diagram showing a shape of outputting four images generated by performing A-D conversion on an output from four linear sensors as the detector in the detecting optical system according to Embodiment 1 of the present invention and analyzing it at each polarization axis and images generated by obtaining the main axis slope and ellipticity of polarized light by polarization operational processing from the A-D converted signal.

Next, any polarization state (a plurality of polarization components) detected by, for example, four linear sensors 30a, 30b, 30c, and 30d configuring each linear sensor arrays 52A to 52E will be described with reference to FIG. 19. Generally, the polarization state is the elliptical polarization, but it becomes the linear polarization or elliptical polarization under specified condition. The important parameter includes a slope ψ of a major axis, ellipticity χ, a length $|E\eta|$ of a long axis of an ellipse, and a length $|E\xi|$ of a short axis of an ellipse. All the polarization state may be represented by the above-mentioned parameters. In order to obtain these parameters, each of the transmission axes 27a, 27b, 27c, and 27d of the polarizing plate shown in FIG. 18(b) is set to, for example, −45°, 45°, 0°, and 90°. Therefore, since (1,1,0), (1,0,1), (1,−1,0), and (1,0,−1) of a stokes vector (however, excepting for elements of circularly polarized light) is obtained. Then, the ellipticity χ, the slope ψ of an ellipse, the length $|E\eta|$ of a long axis of an ellipse, and the length $|E\xi|$ of a short axis of an ellipse are obtained by performing the operational processing with a polarization operational processing circuit 104 (however, a rotational direction of an ellipse cannot be known). In other words, as shown in FIG. 20, it is possible to obtain, for example, an inclined image 44e of a major axis and an ellipticity image 44f that are not obtained from a single analyzation image, in addition to the analyzing axis −45° image 44a, an analyzing axis 45° image 44b, an analyzing axis 0° image 44c, and an analyzing axis 90° image 44d, and increase information quantity obtained by one-time inspection, by transmitting the A-D converting signal of the linear sensors 30a, 30b, 30c, and 30d to the polarization operational processing circuit 104 and performing operational processing when performing A-D conversion on the output from, for example, four linear sensors 30a, 30b, 30c, and 30d configuring each linear sensor array 52A to 52E and generating the image. Further, when the number of angles of the analyzing axis (transmission axis) is reduced, the information quantity obtained by one-time inspection is also reduced.

Figure 21:
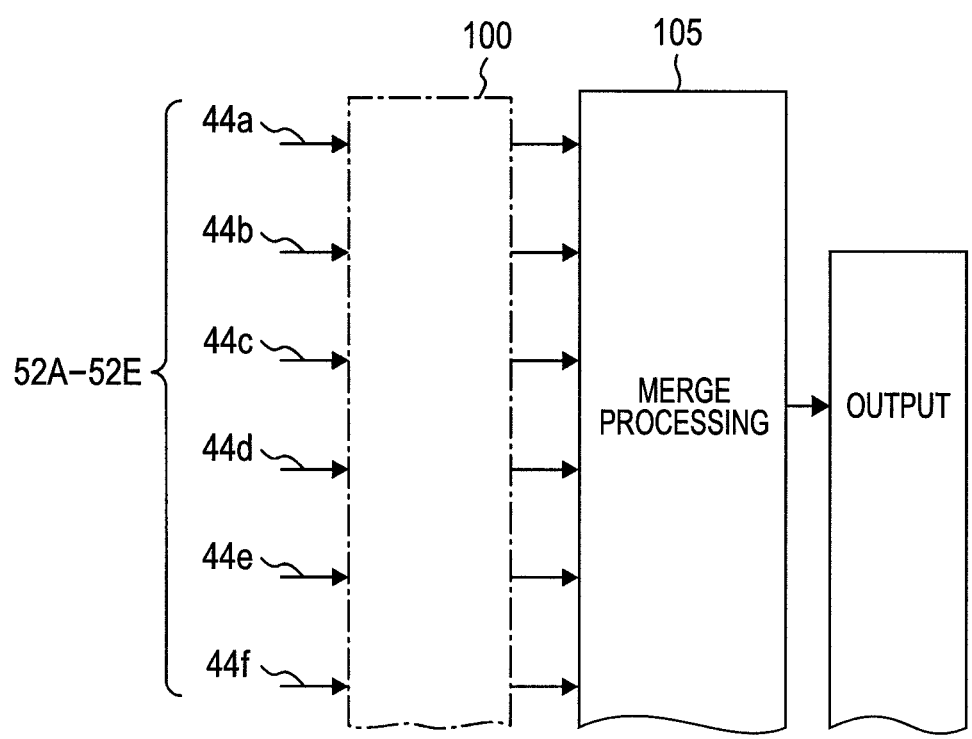
FIG. 21 is a diagram showing a function of merging and outputting results obtained by processing each image having six different quantities (for example, polarization components) in a signal processing unit according to Embodiment 1 of the present invention.

As described above, each of the images 44a to 44f obtained corresponding to each linear sensor arrays 52A to 52E is individually subjected to the signal processing in the signal processing unit 100 shown in FIG. 21 to determine the defects. Thereafter, a merge processing circuit 105 may merges and outputs the defect decision results. Further, the signal processing unit 100 is configured as specifically shown in FIGS. 22A to 22D.

The signal processing unit 100a shown in FIG. 22A performs the die comparison processing as the signal processing condition. In other words, when any die images (for example, 44a to 44f) obtained from each linear sensor array 52A to 52E are stored in a delay memory 32 and the adjacent die images (for example, 44a to 44f) is captured, in order to correct the position misalignment due to vibration, etc., a position alignment circuit 33 performs a position alignment and a subtraction circuit 34 performs subtraction processing on the obtained images. A memory 35 stores the images that are position-aligned in parallel and a threshold value processing circuit 36 calculates a threshold value. A comparison circuit 37 performs comparison processing on the subtraction-processed signal and the threshold value and a defect decision unit 38 extracts a foreign material signal or a defect signal. The extracted foreign material or defect signals are output as a defect map as they are or are classified according to a foreign material kind and defect kind by a classification and sizing processor 39 and a size of foreign material or defect are obtained.

The signal processing unit 100b shown in FIG. 22B performs the cell comparison processing as the signal processing condition. In other words, when the images (for example, 44a to 44f) obtained from each linear sensor array 52A to 52E include the signal obtained from the pattern having the same shape, an image shift circuit 40 shifts the images and the position alignment circuit 33 performs the position alignment in order to obtain the corresponding points of the images before and after the shift and the subtraction circuit 34 performs the subtraction processing on the obtained image. The memory 35 stores the images that are position-aligned in parallel and the threshold value processing circuit 36 calculates a threshold value. The comparison circuit 37 performs the comparison processing on the subtraction-processed signal and the threshold value and the defect decision unit 38 extracts the foreign material signal or the defect signal. The extracted foreign material and defect signals are output as the defect map as they are or foreign material kind and defect kind is classified and a size of foreign material or defect are obtained, by a classification and sizing processor 39.

Figure 22C:
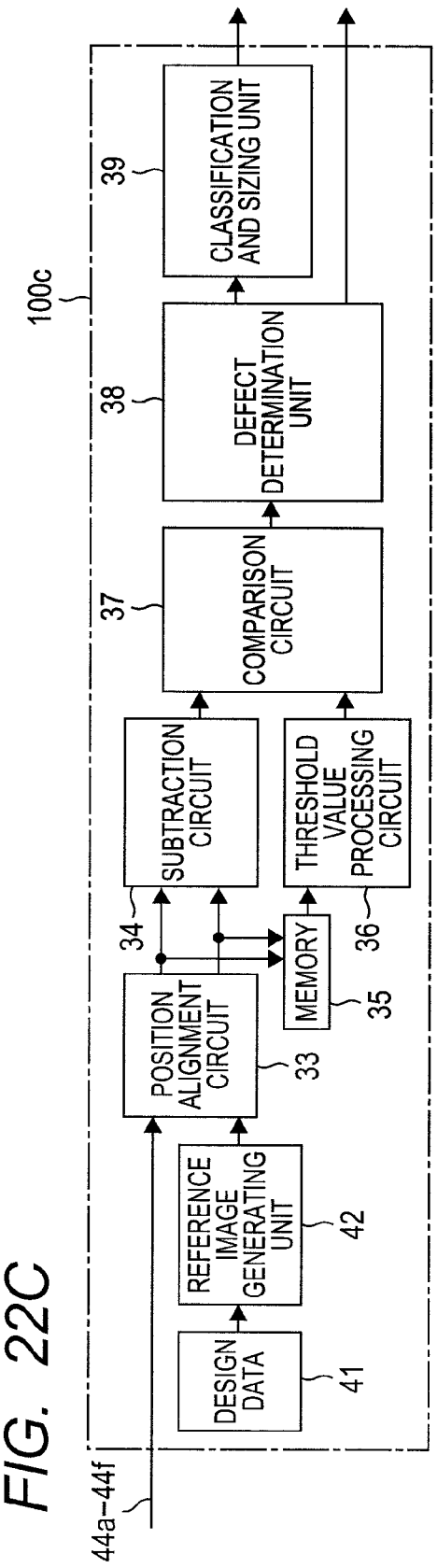
FIG. 22C is a diagram showing a configuration, where design data comparison processing as signal processing conditions is executed, in the signal processing unit according to Embodiment 1 of the present invention.

The signal processing unit 100c shown in FIG. 22C performs the design data comparison processing as the signal processing condition. In other words, the design data obtained from the design data 41 is transmitted to a reference image generator 42 to generate a reference image. The reference image is subjected to the position alignment in order to obtain the corresponding points to the real images (for example, 44a to 44f) obtained from each linear sensor array 52A to 52E and the subtraction circuit 34 performs the subtraction processing on the obtained images. The memory 35 stores the images that are position-aligned in parallel and the threshold value processing circuit 36 calculates a threshold value. The comparison circuit 37 performs the comparison processing on the subtraction-processed signal and the threshold value and the defect decision unit 38 extracts the foreign material signal or the defect signal. The extracted foreign material and defect signals are output as the defect map as they are or foreign material kind and defect kind is classified and a size of foreign material or defect are obtained, by a classification and sizing processor 39.

Figure 22D:
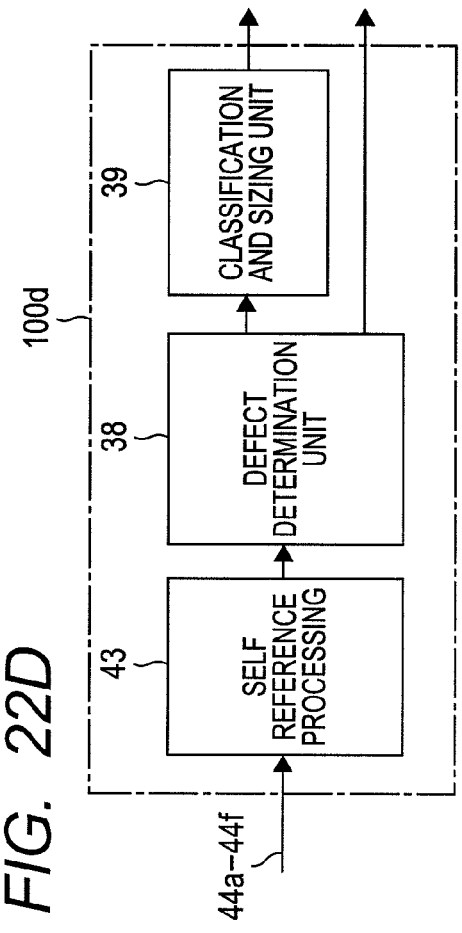
FIG. 22D is a diagram showing a configuration, where a self-reference scheme as signal processing conditions is executed, in the signal processing unit according to Embodiment 1 of the present invention.

The signal processing unit 100d shown in FIG. 22D performs the self reference scheme as the signal processing condition. In other words, it determines defects by searching a similar pattern among the images (for example, 44a to 44f) obtained from each linear sensor array 52A to 52E and performing the comparison processing on a group of the similar patterns or determines defects based on feature quantity of the pattern and a defect candidate.

The signal processing unit 100 performs the processing scheme so called golden image comparison as other signal processing condition that is not shown.

Figure 23:
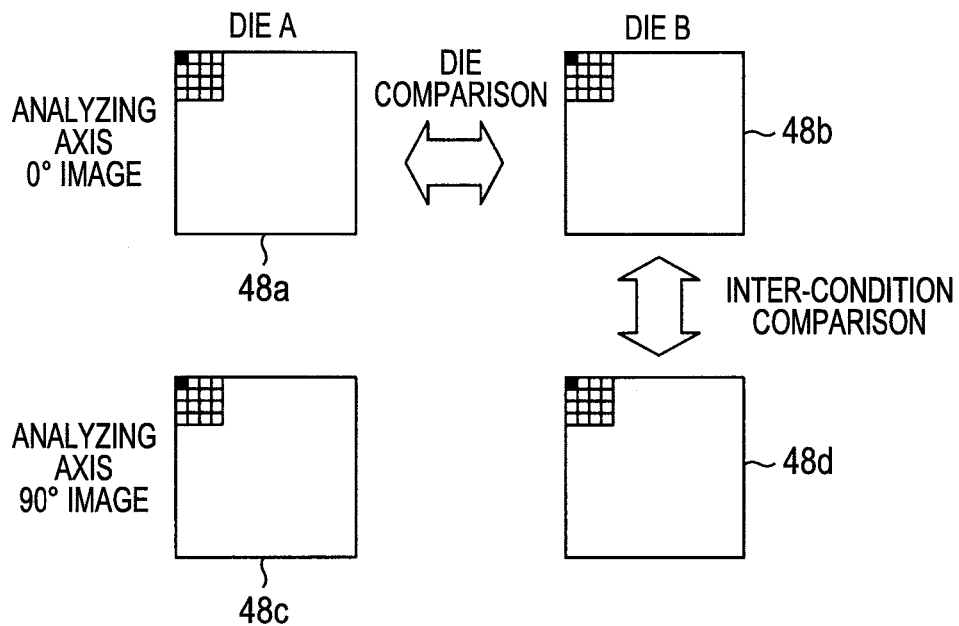
FIG. 23 is a diagram showing a case where the images are compared under different optical conditions (for example, detection conditions such as polarization components) in a group of the same dies, in addition the die comparison in the signal processing unit according to Embodiment 1 of the present invention.

Further, as shown in FIG. 23, the signal processing unit 100 may perform the comparison processing to a group of the images 48a and 48c; 48b and 48d obtained under different conditions (detection condition and/or illuminating condition) between the same dies, in addition to the die comparison comparing a group of the images 48a and 48b obtained from different dies under the same conditions (for example, the same analyzing axis angle).

Figure 24:
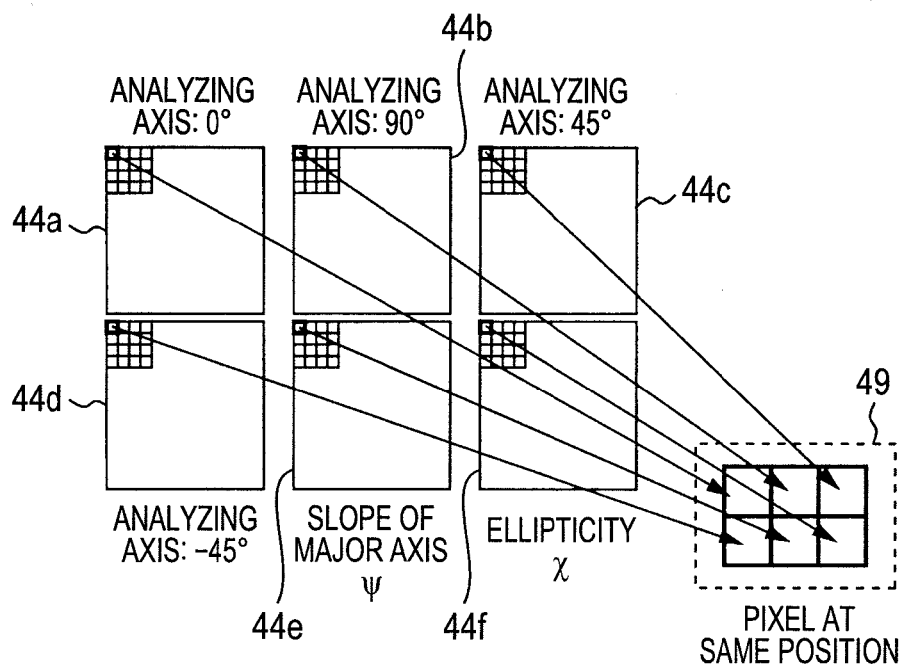
FIG. 24 is a diagram showing a shape where signals of corresponding pixels are taken out from a plurality of images having different optical conditions (for example, detection conditions such as polarization components) and new images are generated, in the signal processing unit according to Embodiment 1 of the present invention.

Further, as shown in FIG. 24, the signal processing unit 100 may collects and arranges the signals of the corresponding point (a point corresponding to the same place of the semiconductor waver W) of, for example, six kinds of images 44a, 44b, 44c, 44d, 44e, and 44f obtained from different detection conditions (for example, an angle of analyzing axis, a slope $\psi$ of a major axis, ellipticity $\chi$) and/or illuminating condition (for example, illuminating orientation $\phi$) to generate a new image 49 showing the difference for points corresponding to 1 pixel on the semiconductor wafer W under different conditions, may determine the defects by performing the die comparison on the image 49 (not shown), or may perform the defect decision (self reference processing) by extracting the feature quantity of the image 49 itself (not shown). Further, it is no wonder that the cell comparison, the design data comparison, Golden image comparison can also be used, without being limited to the die comparison.

Figure 25:
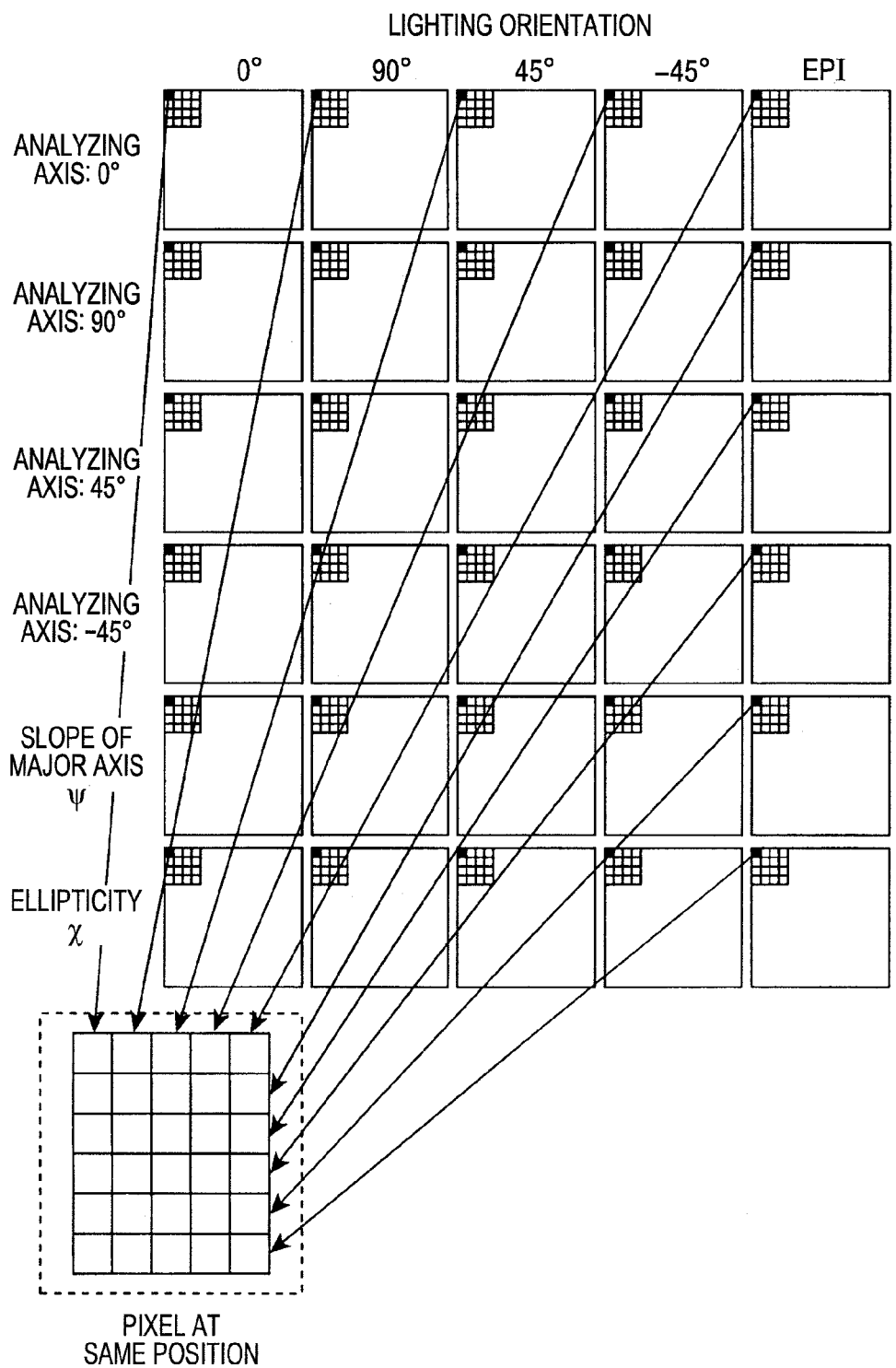
FIG. 25 is a diagram showing a shape where signals of corresponding pixels are taken out from a plurality of images having 30 different optical conditions (for example, a combination of illuminating conditions such as illuminating orientation and detection conditions such as polarization components) and new images are generated, in the signal processing unit according to Embodiment 1 of the present invention.

Further, as shown in FIG. 25, the signal processing unit 100 collects and arranges a signal obtained from any one point (specifically, a region corresponding to 1 pixel) on, for example, the semiconductor wafer W to obtain thirty kinds of information obtained by multiplying six kinds of different detection conditions (for example, an angle of analyzing axis, a slope $\psi$ of a major axis, ellipticity $\chi$) by five kinds of illuminating condition (for example, illuminating orientation $\phi$) and since the information quantity is dramatically increased, it is expected that sensitivity and supplementary rate are further increased and the classification and sizing accuracy are improved.

Figure 26:
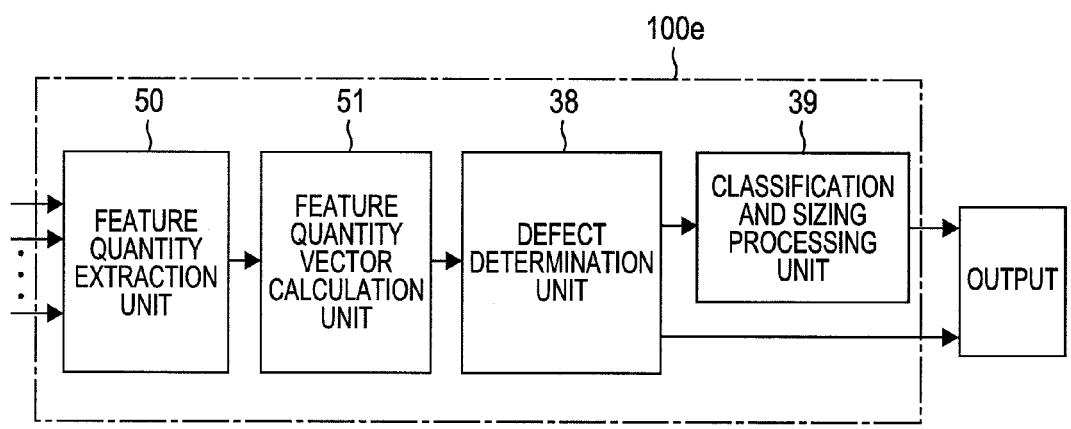
FIG. 26 is a diagram showing a function of performing defect decision, classification, sizing processing by using vectors of feature quantity in the signal processing unit according to Embodiment 1 of the present invention and outputting the results.
Figure 27A:
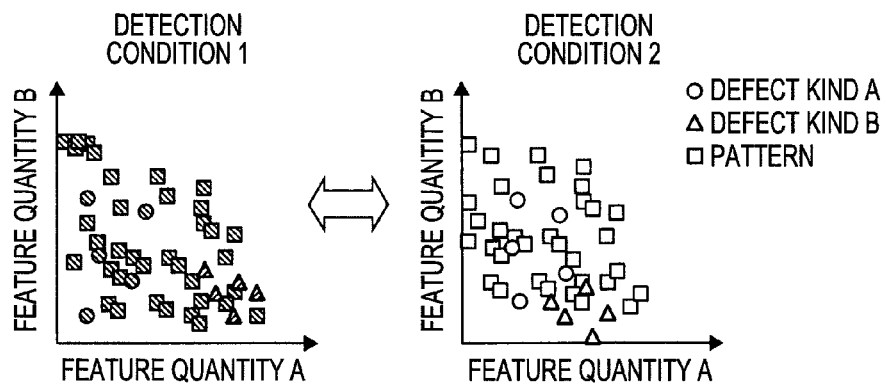
FIG. 27A is a diagram calculating a feature quantity A and a feature quantity B of a signal and plotting the calculated signal onto a space of the feature quantity A and the feature quantity B, for the image under the detection condition 1 and plotting a signal obtained by calculating the feature quantity A and the feature quantity B of the signal onto the space of the feature quantity A and the feature quantity B, for the image under the detection condition 2.
Figure 27B:
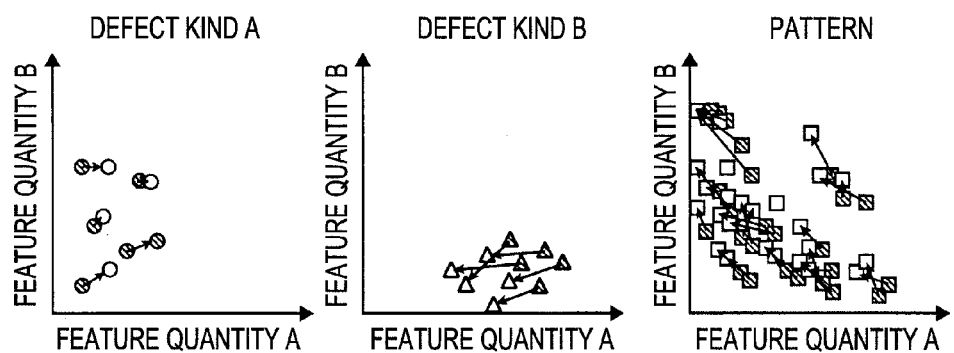
FIG. 27B is a graph representing by vectors variation of each plot point calculated by a vector calculating unit of the feature quantity in the case where the detection condition is changed from 1 into 2 and FIG. 27C is a diagram plotting the obtained vectors as a change in the feature quantity A to the change in the feature quantity B.
Figure 27C:
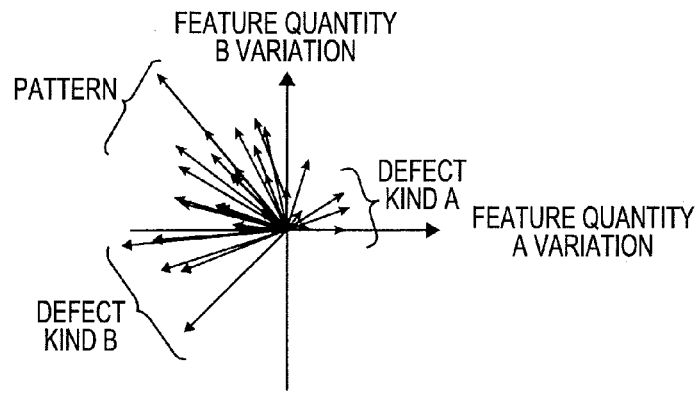

Further, the signal processing unit 100e shown in FIG. 26 may extract defects in consideration of vector action of the feature quantity (contrast or total luminance, etc.) between conditions (detection condition and illumination condition) as the signal processing condition. In other words, as shown in FIG. 27A, a feature quantity extracting unit 50 calculates a feature quantity A and a feature quantity B of signal for an image (for example, analyzing axis −45° image 44a) under certain detection condition 1 and plots the calculated signal to a space defined by the feature quantity A and the feature quantity B. At this time, a defect kind A, a defect kind B, and a pattern that is a non-defect are mixed in a space of a feature quantity, such that defects cannot be exposed. Next, the feature quantity extracting unit 50 similarly calculates the feature quantity A and the feature quantity B of a signal for an image (for example, analyzing axis 45° image 44a) under certain detection condition 2 and plots the calculated signal to a space of the feature quantity A and the feature quantity B. Further, when representing the variation quantity of each plot points, when the detection condition is changed from the detection condition 1 to the detection condition 2, in vector by calculating the quantity variation with a feature quantity vector calculation unit 51, this is as shown in FIG. 27B. Finally, it is possible to separate the defect kind A, the defect kind B, and the pattern that is a non-defect as shown in FIG. 27C by plotting the obtained vector as the change in feature quantity A against the change in feature quantity B and the defects. Thus, a defect which cannot be detected under the single condition, can also be detected in a defect determining unit 38. As a result, the defect determining unit 38 outputs the extracted defect signal as the defect map as it is or foreign material kind and defect kind is classified and a size of foreign material or defect are obtained, by a classification and sizing processor 39.

The signal processing unit 100 (100a to 100e) configured as described above is connected to a computer 101 having an processor element 1011, a memory device 1012, etc., thereby making it possible to set and change parameters, etc., from the outside, as shown in FIG. 1. Further, external devices 103 such as a mouse, a keyboard, a printer are connected to the computer 101.

Figure 28:
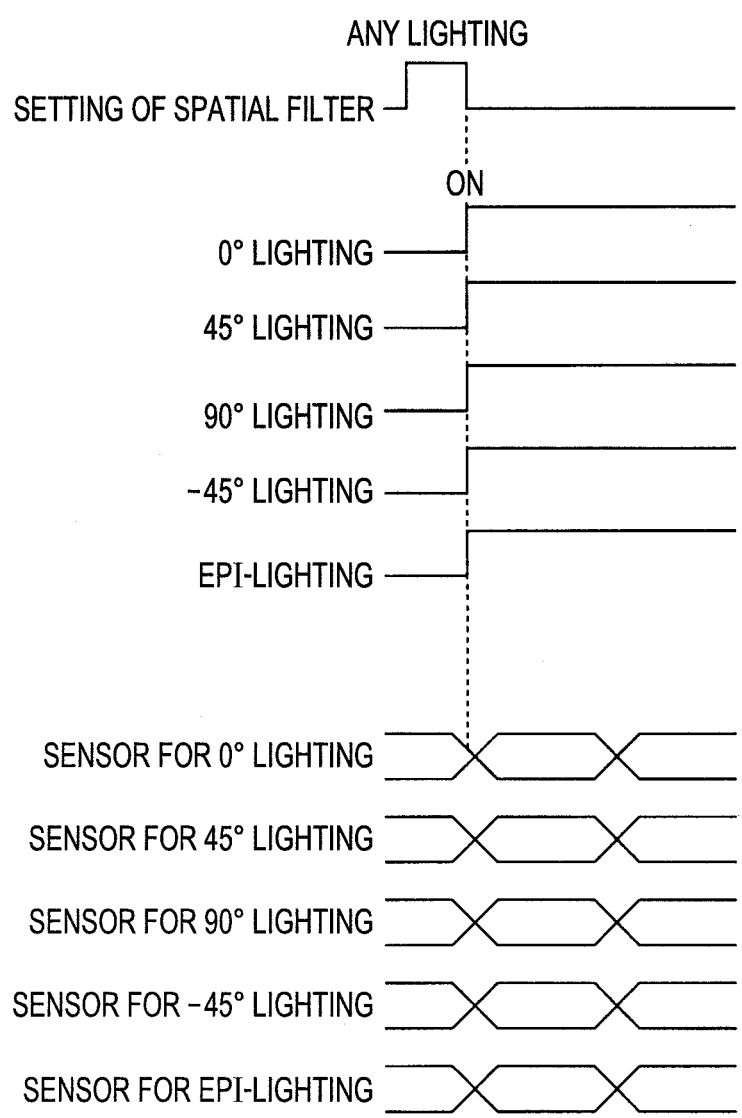
FIG. 28 is a diagram showing a setting of a spatial filter, illuminating, and timings of imaging by a sensor in Embodiment 1 of the present invention.
Figure 29A:
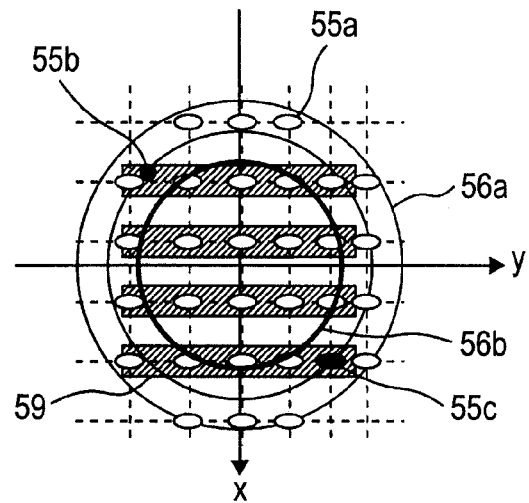
FIG. 29A is a diagram showing a shape of an imaging of diffracted light from a repetitive pattern at an exit pupil of an objective lens (Fourier transformation plane) in the detecting optical system according to Embodiment 1 of the present invention.
Figure 29B:
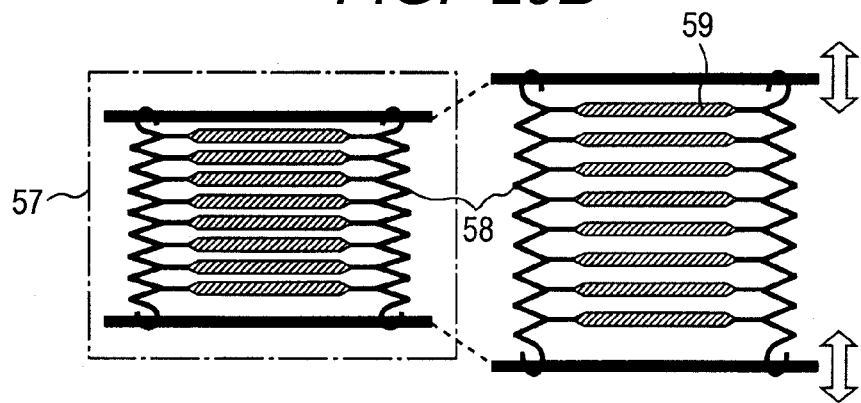
FIG. 29B shows a spatial filter for shielding light at a plurality of plate-like light shielding plates 59 disposed in a line.
Figure 29C:
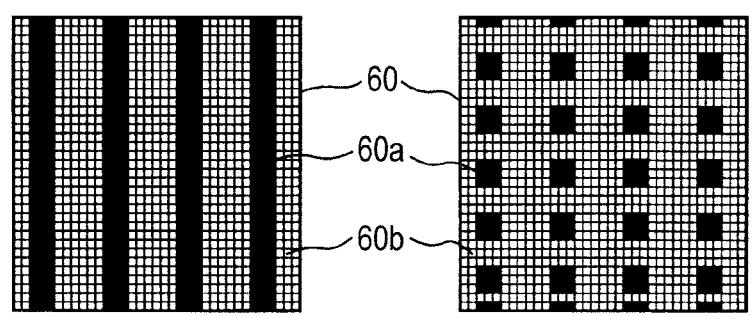
FIG. 29C shows a spatial filter in which the shape of the light shielding unit may be optionally selected.

Next, the setting of the spatial filter 28, the illuminating timing at each illumination azimuth angle, and an operation timing of each line sensor array 52A to 52E will be described with reference to FIG. 28. In Embodiment 1, the shape of the light shielding unit of the spatial filter 28 is fixed. A diffracted image 55a obtained by a repetitive pattern on the Fourier transformation plane is imaged regularly as shown in FIG. 29A. In the this embodiment, the illuminated beam is a parallel light in a y-axis direction and the condensed linear beams 300a to 300e in an x-axis direction, such that the diffracted image 55a obtained by the repetitive pattern on the Fourier transformation plane is expanded by illuminating NA in an x-axis direction. Further, reference numeral 55*b* represents irradiated light, reference numeral 55*c* represents zero-order diffracted light (regular reflected light), reference numeral 56*a* represents a pupil diameter corresponding to NA 1.0, and reference numeral 56*b* represents a pupil diameter corresponding to detection NA. The diffracted lights may shield light by arranging a plurality of plate-like light shielding plates 59 as shown in FIG. 29B. At this time, if the pitch of the light shielding plate 59 is configured to be varied by a spring 58, it can be used to seal plural pitches of light patterns formed by the diffracted lights corresponding to the repetitive pattern of plural pitches. However, in Embodiment 1, since there are, for example, five illuminations Ia to Ie, five diffraction patterns are present on the Fourier transformation plate. For this reason, in the configuration as shown in FIG. 29B, it is difficult to effectively shield the entire diffracted light. In this case, as shown in FIG. 29C, it is preferable to use the spatial filter by which the shape of the light shielding part can be selected optionally. A liquid crystal device or a digital micro device (DMD) can be used for the spatial filter.

Figure 30:
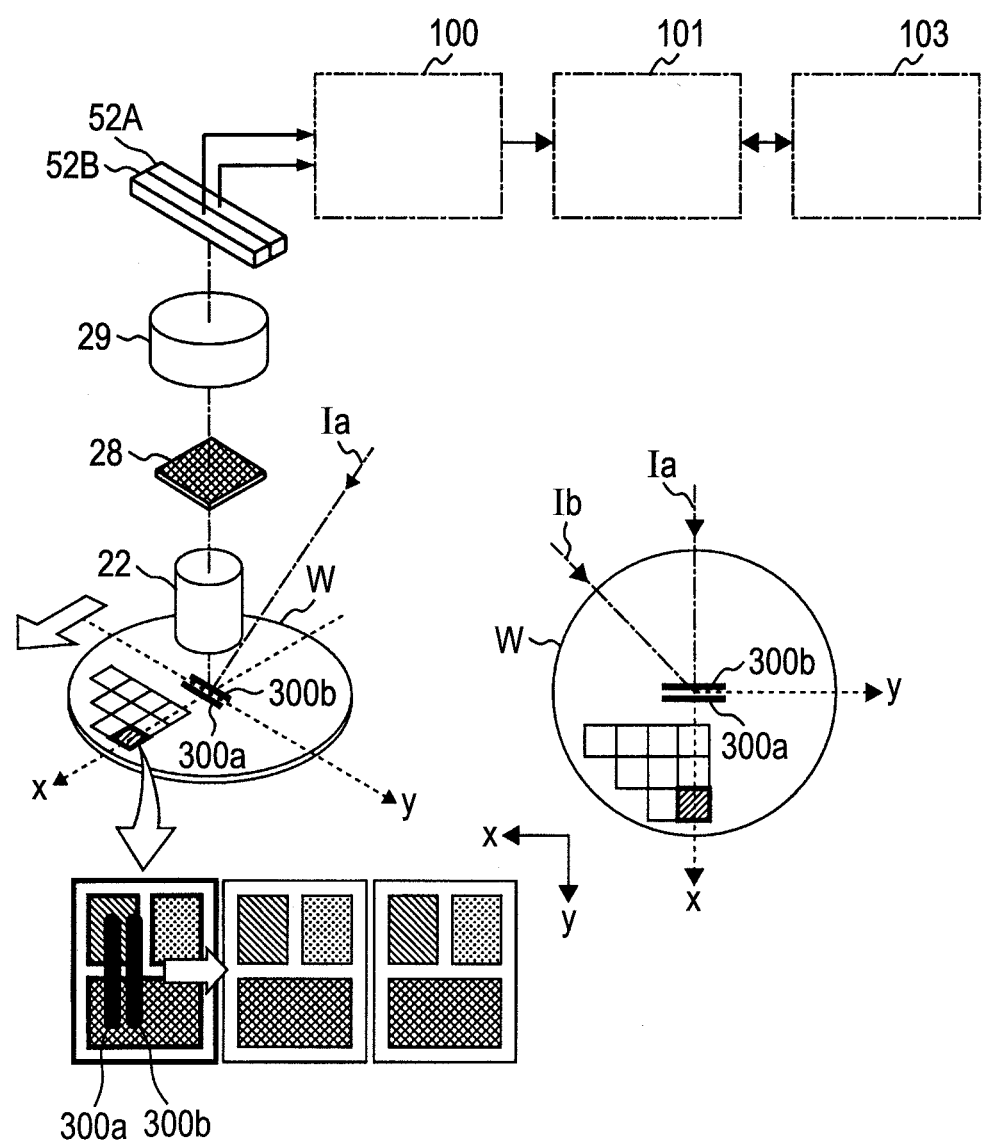
FIG. 30 is a perspective view showing a schematic configuration of a modified example of a defect inspection device according to Embodiment 1 of the present invention.

In addition, in Embodiment 1 of the present invention, the illumination optical system 200 is not limited to five kinds as the illuminating orientation but, as shown in FIG. 30, may includes a plurality of illuminating orientations. Further, in the detecting optical system 400, the polarization state included in each linear array sensor 52 is not limited to four kinds, but the polarization state may also be in plural, including the polarization arithmetic processing circuit 104.

Embodiment 2

A defect inspection method and a defect inspection device according to Embodiment 2 of the present invention will be described with reference to FIGS. 31 to 36.

Figure 31A:
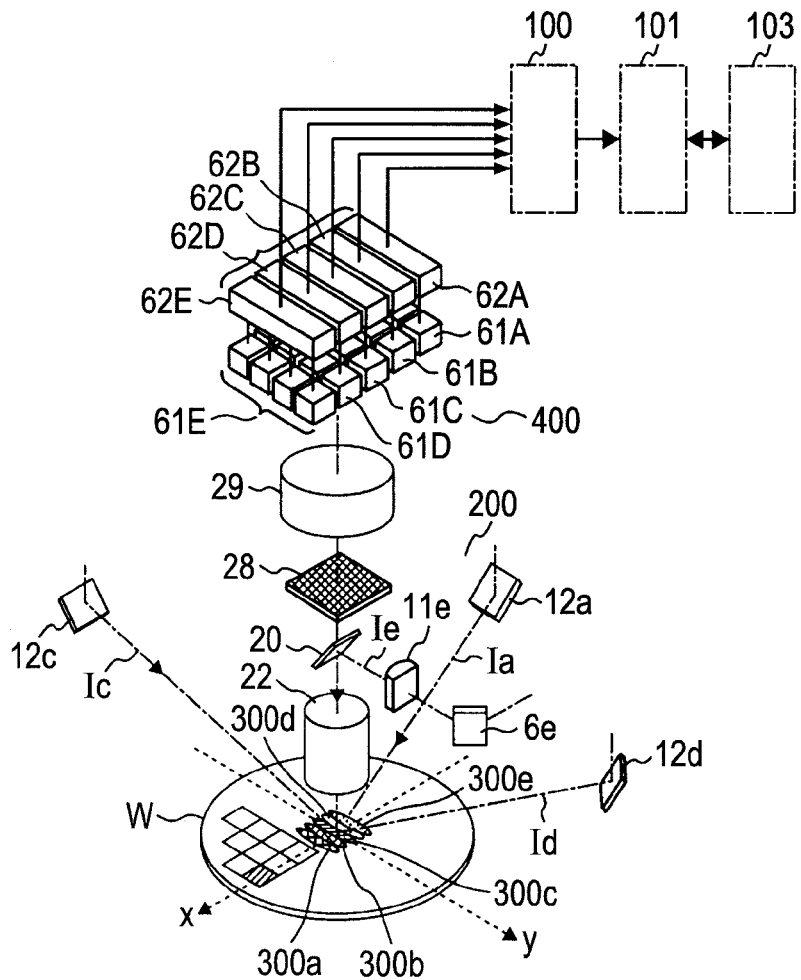
FIG. 31A is a perspective view showing a schematic configuration of the defect inspection device according to Embodiment 2 of the present invention and FIG. 31B is a diagram showing a pixel of an area sensor array projected onto the semiconductor wafer W.
Figure 31B:
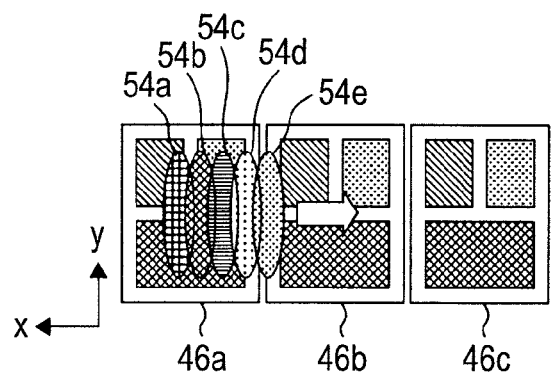
Figure 32:
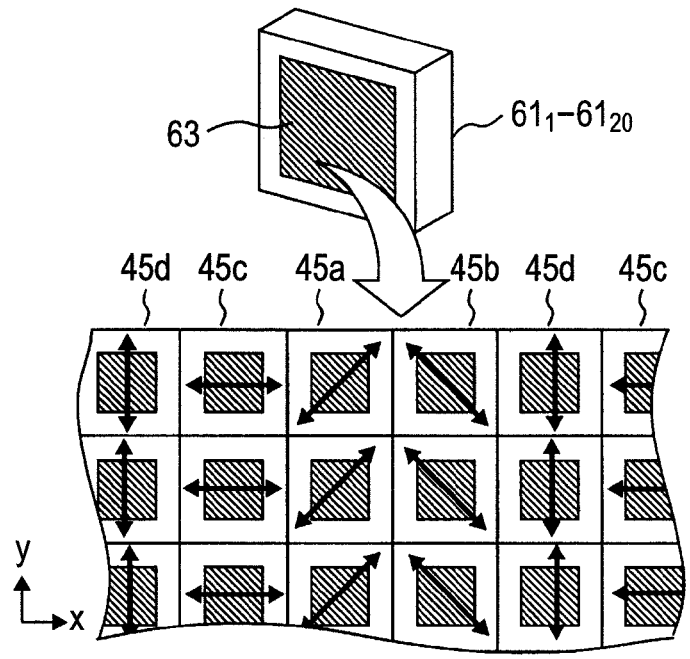
FIG. 32 is a diagram showing the area sensor as the detector where a polarizing film is attached to each pixel in the detecting optical system according to Embodiment 2 of the present invention.
Figure 33:
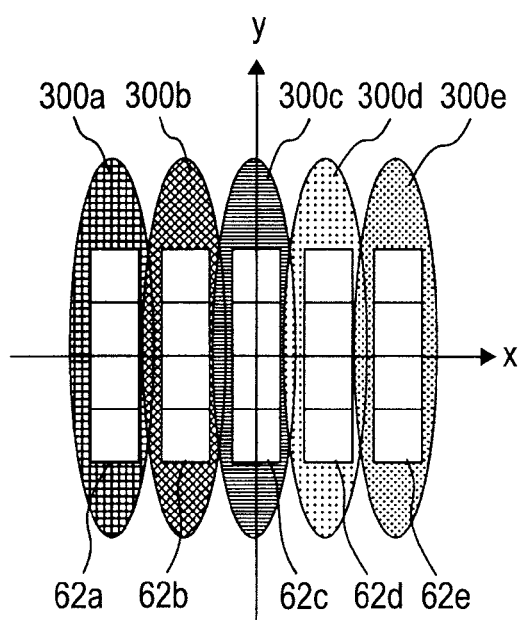
FIG. 33 is a diagram showing an illuminating area on the sample and a pixel projected onto the sample in Embodiment 2 of the present invention.

FIG. 31 is a perspective view showing a schematic configuration of a defect inspection apparatus according to Embodiment 2 of the present invention. In other words, Embodiment 2 is different from Embodiment 1 in that the detecting optical system 400 uses area sensor arrays 61A to 61E and image coupling processors 62A to 62E, instead of using the linear sensor arrays 52A to 52E. In Embodiment 2, each area sensor array 61A to 61E is configured by arranging four area sensors 61Aa to 61Ad, 61Ba to 61Bd, 61Ca to 61Cd, 61Da to 61Dd, and 61Ea to 61Ed for each illuminating orientation and the entire area sensor array is configured to include a total of twenty area sensors $61_1$ to $61_{20}$ that are arranged two-dimensionally. A light receiving unit 63 of each area sensor $61_1$ to $61_{20}$ is attached with pixels 45*a*, 45*b*, 45*c*, and 45*d* of a polarizing film having different transmission axis for each pixel column, as shown in FIG. 32. Thereby, it is possible to detect the scattered light from the semiconductor waver W in the same state as the linear sensor array described in Embodiment 1. Further, as shown in FIG. 33, if detection magnification is set so that the pixels 62*a*, 62*b*, 62*c*, 62*d*, and 62*e* of the linear sensor array projected onto the semiconductor wafer W is in the range of the spot size of each of linear beams 300*a*, 300*b*, 300*c*, 300*d*, and 300*e*, it is possible to collectively detect the diffracted and scattered light generated from each linear region irradiated under different illuminating condition and signals are analyzed at different polarization axes (analyzing axis). In other words, it is possible to obtain, for example, the inclined image 44*e* of a major axis and the ellipticity $\chi$ image 44*f* that are not obtained from a single analyzation image, in addition to an analyzing axis −45° image 44*a*, an analyzing axis 45° image 44*b*, an analyzing axis 0° image 44*c*, and an analyzing axis 90° image 44*d*, and increase information quantity obtained by one-time inspection, by transmitting the A-D converting signal including the analyzing axis −45° image 44*a*, the analyzing axis 45° image 44*b*, the analyzing axis 0° image 44*c*, and the analyzing axis 90° image 44*d* to the polarization operational processing circuit 104 and performing operational processing, as shown in FIG. 20, when performing the A-D conversion on the output from, for example, the pixel columns 62*a* to 62*e* of four area sensor arrays configuring each area sensor array 61A to 61E and generating the image.

Figure 34:
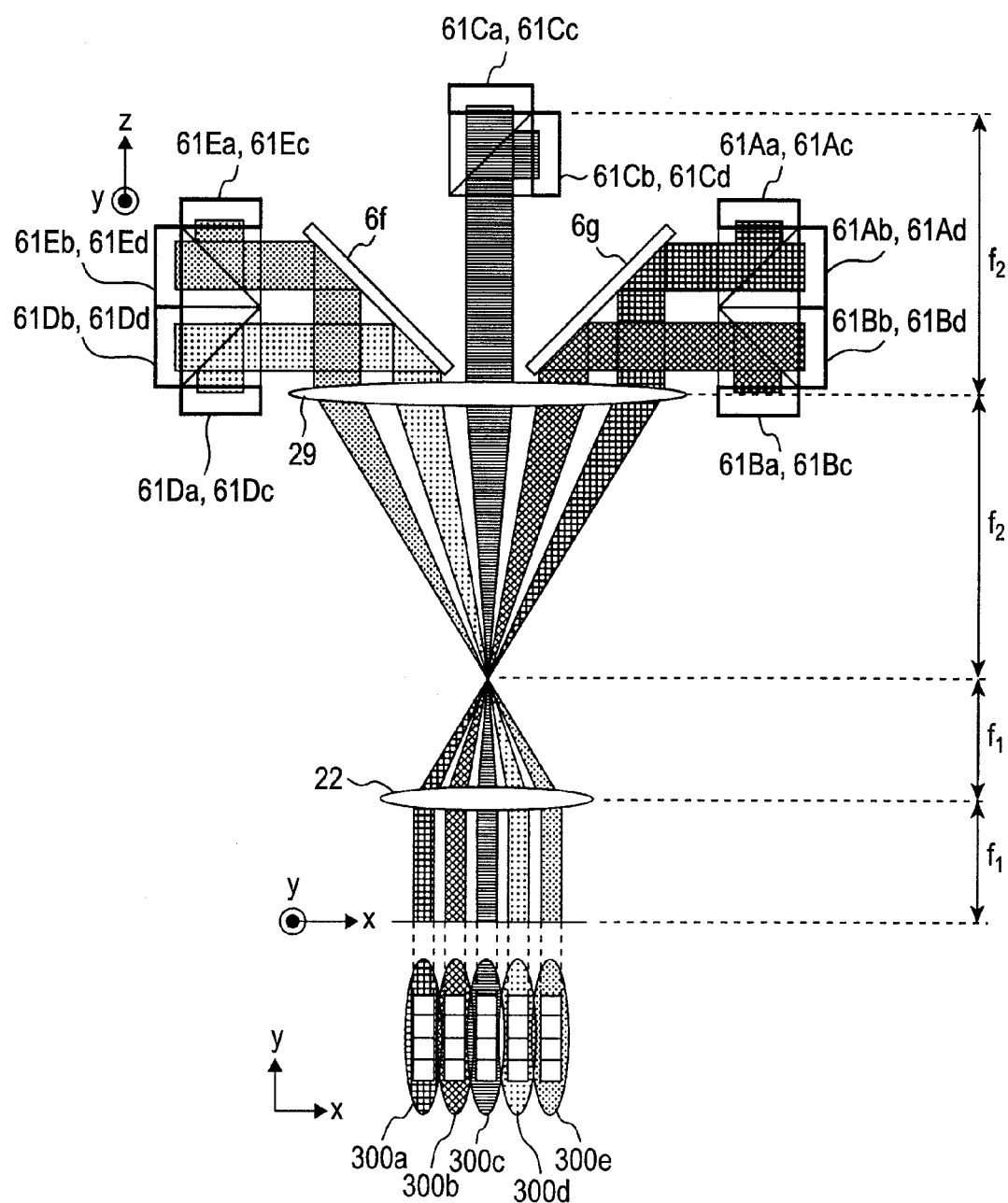
FIG. 34 is a diagram showing a separate implementation form in the detecting optical system according to Embodiment 2 of the present invention.
Figure 35A:
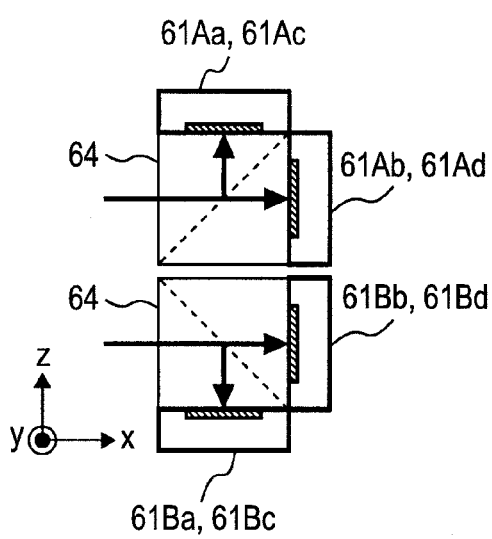
FIG. 35A is an enlarged diagram of the area sensor in the configuration shown in FIG. 34 as a separate implementation form in the detecting optical system according to Embodiment 2 of the present invention.
Figure 35B:
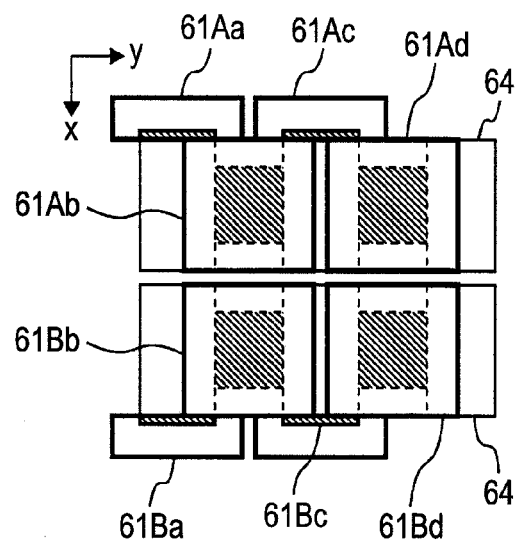
FIG. 35B is a diagram showing a configuration where effective pixel areas of adjacent area sensors are disposed in a line without a gap.
Figure 35C:
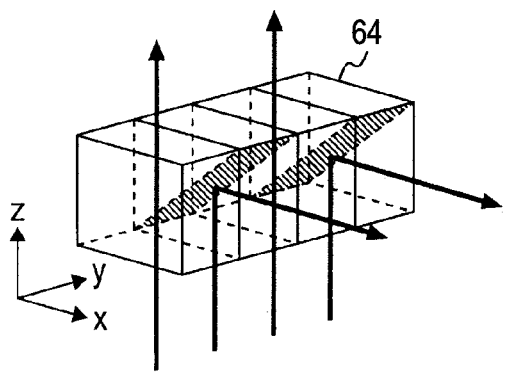
FIG. 35C is a perspective view of a light path branching element in which a transmission part and a reflection part are alternately disposed.

In this case, as shown in FIG. 31, there is a case where it is impossible to implement the high-density mounting only by arranging twenty area sensors in a unit plane shape. In the case, it is preferable to implement the mounting as shown in FIGS. 34, 35A, 35B and 35C. In other words, as shown in FIG. 34, the light path is branched into three by using mirrors 6*f* and 6*g* and as shown in FIGS. 35A and 35C, in each of three branched light paths, it is alternately branched into the transmission light and the reflected light by using a light path branch element 64 so that the transmission unit and the reflection unit are alternately present. The effective pixel regions of the adjacent area sensors, as shown in FIG. 35B, can be arranged without a gap by a configuration receiving the branched reflected light in the area sensors 61Aa, 61Ac; 61Ba, 61Bc; 61Ca, 61Cc; 61Da, 61Dc; and 61Ea, 61Ec and the branched transmission light in the area sensors 61Ab, 61Ad; 61Bb, 61Bd; 61Cb, 61Cd; 61Db, 61Dd; and 61Eb, 61Ed.

Figure 36:
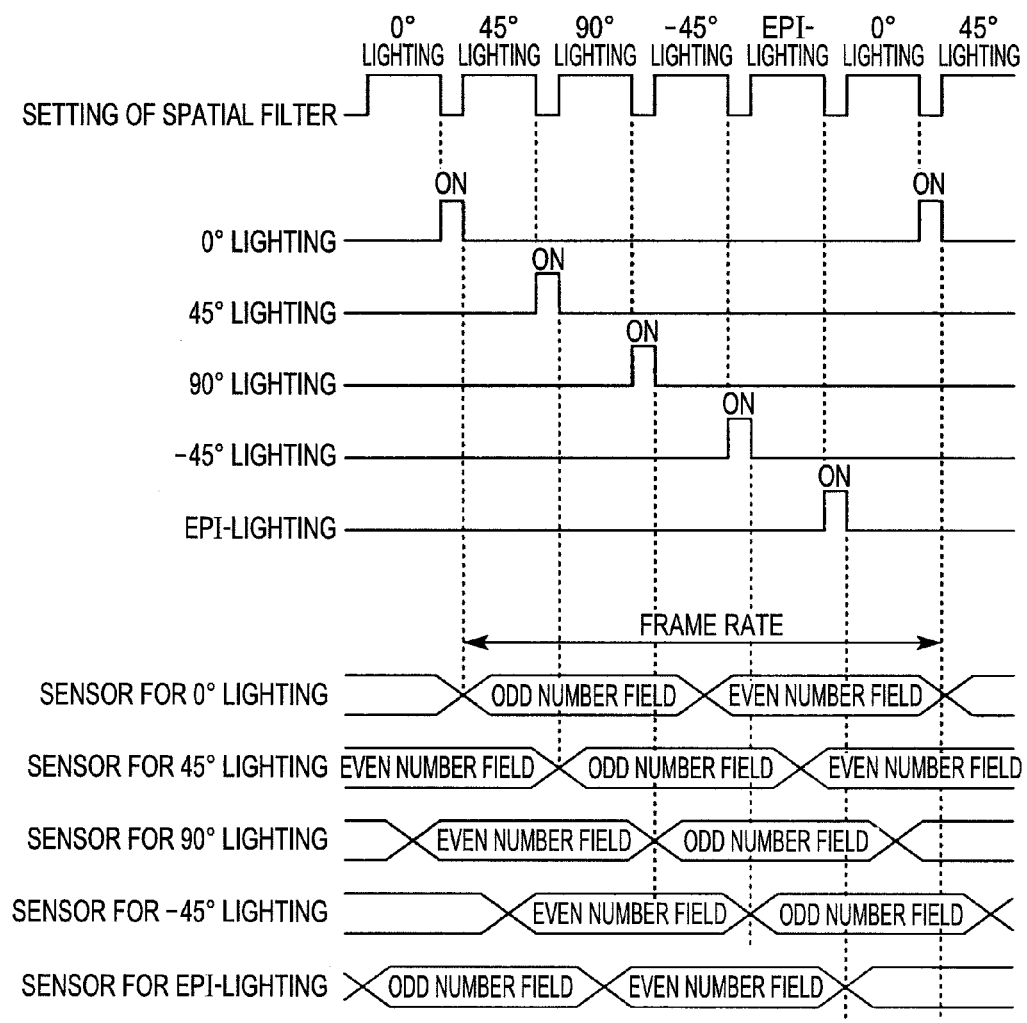
FIG. 36 is a diagram showing a setting of a spatial filter, illuminating, and timings of imaging by a sensor in Embodiment 2 of the present invention.

Next, the setting of the spatial filter 28, the illumination timing at each illuminating azimuth angle, and an operation timing of each area sensor array 61A to 61E will be described with reference to FIG. 36. Since a number of area sensors are operated at several tens of frames per second, the operational speed is relatively low as compared to that of the linear sensor. In Embodiment 2, the illumination of each azimuth angle is performed as strobe illumination, and the illumination onto the semiconductor wafer W is switched by the azimuth angle. In other words, the light shielding pattern of the spatial filter 28 for the 0° illumination is set first. Shortly after that, the 0° illumination is performed. At the same time, the transmission of the data is started in the area sensor array 61A for 0° illumination. The illuminating time is preferable to set within a period that the semiconductor wafer W, which is the inspection object, moves in a region which is approximately ⅕ to ½ of the pixel size projected onto the semiconductor wafer W. Thereby, it is possible to prevent the image from being smoothed in the scanning direction of the semiconductor wafer W. For Example, when the throughput is implemented similar to Embodiment 1 in the case where the pixel size of the area sensor is 10 μm and the detection magnification is five times (that is, the pixel size projected onto the semiconductor wafer W is 2 μm), since the scanning rate is 9.1 mm/s, it is preferable that the illuminating time is set 0.21 ms. Since the frame rate of the conventional area sensor is 30 frames per second, that is, a time required to transmit all the data is 33.3 ms, above illuminating time is only a part time of the frame rate. Further, the light shielding pattern of the spatial filter 28 for the 45° illumination is set at the same time when the 0° illuminating is completed. Shortly after that, the 45° illuminating is performed. At the same time, the transmission of the data is started in the area sensor array 61B for the 45° illumination. Next, the light shielding pattern of the spatial filter 28 for the 90° illumination is set at the same time when the 45° illumination is completed. Shortly after that, the 90° illuminating is performed. At the same time, the transmission of the data is started in the area sensor array 61C for the 90° illumination. Continuously, the light shielding pattern of the spatial filter 28 for the −45° illumination is set at the same time when the 90° illumination is completed. Shortly after that, the −45° illumination is performed. At the same time, the transmission of the data is started in the area sensor array 61C for the 45° illumination. Finally, the light shielding pattern of the spatial filter 28 for the epi-illumination is set at the same time when the −45° illumination is completed. Shortly after that, the epi-illumination is performed and at the same time, the transmission of the data is started in the area sensor array 61E for the epi-illumination. As described above, the operation is sequentially repeated while scanning the stage, such that the entire surface of the semiconductor wafer W can be inspected.

Embodiment 3

Figure 37:
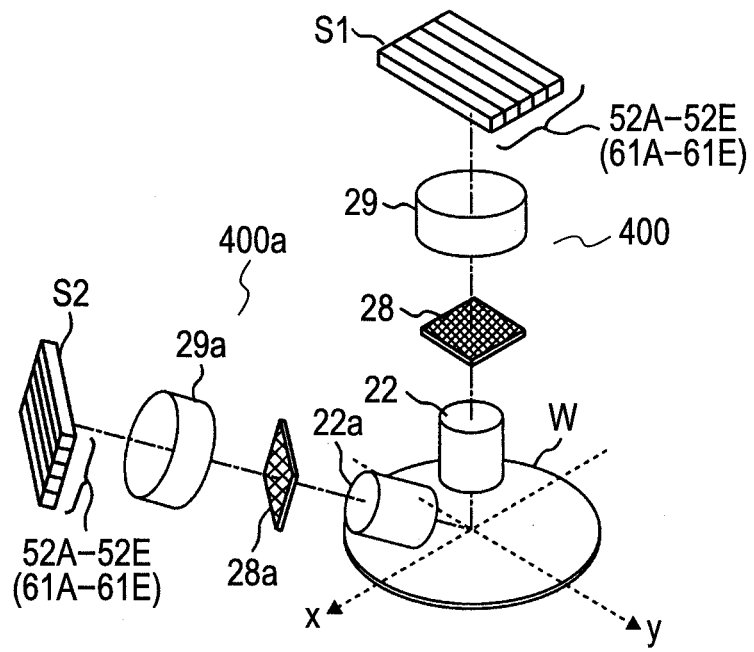
FIG. 37 is a perspective view showing a schematic configuration of a detecting optical system in a defect inspection device according to Embodiment 3 of the present invention.
Figure 38:
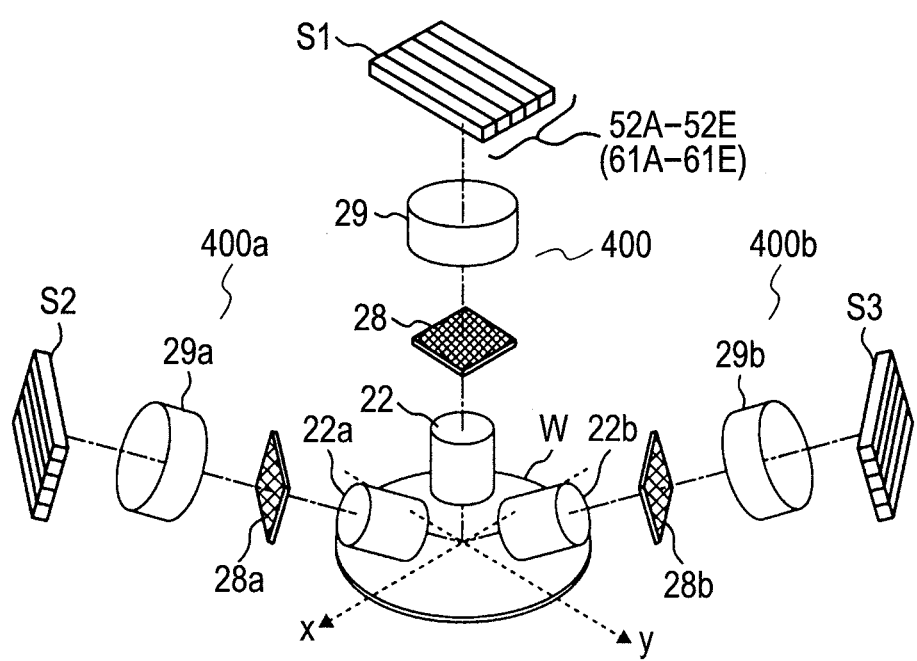
FIG. 38 is a diagram showing a schematic configuration of the detecting optical system different from FIG. 37.

Next, Embodiment 3 of the present invention will be described with reference to FIGS. 37 and 38. Embodiment 3 shown in FIG. 37 adds an oblique detecting system 400a (configured to include the objective lens 22a, the spatial filter 28a, the imaging lens 29a, and the detector S2, etc.) to the first and Embodiment 2s in order to increase the optical conditions. Since other functions and components thereof are the same as the first and the second Embodiments, therefore the description thereof will be omitted. Embodiment 3 shown in FIG. 38 adds another oblique detecting system 400b (configured to include the objective lens 22b, the spatial filter 28b, the imaging lens 29b, and the detector S2, etc.). Since other functions and components thereof are the same as the first and second Embodiments, therefore, the description thereof will be omitted.

As described above, the defect inspection device according to the Embodiment 3 adds the oblique detecting optical system to the defect inspection device explained in the first and the second embodiments. Since the information quantity is further increased comparing to that of the first and the second embodiment, it is expected that sensitivity and supplementary rate are further increased and the classification and sizing accuracy are improved.

Embodiment 4

Figure 39:
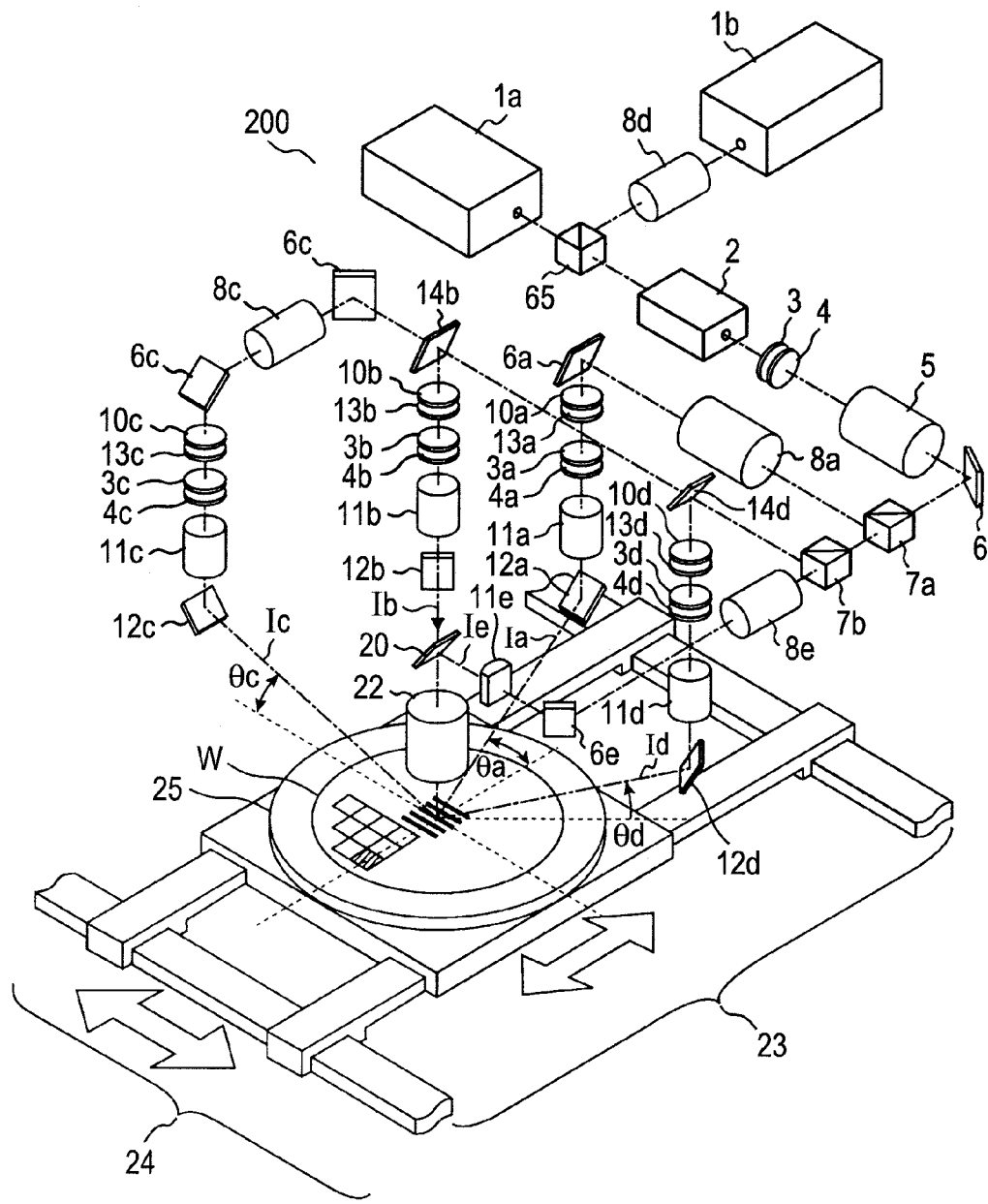
FIG. 39 is a diagram showing a configuration other than a detecting optical system in a defect inspection device according to Embodiment 4 of the present invention.
Figure 40:
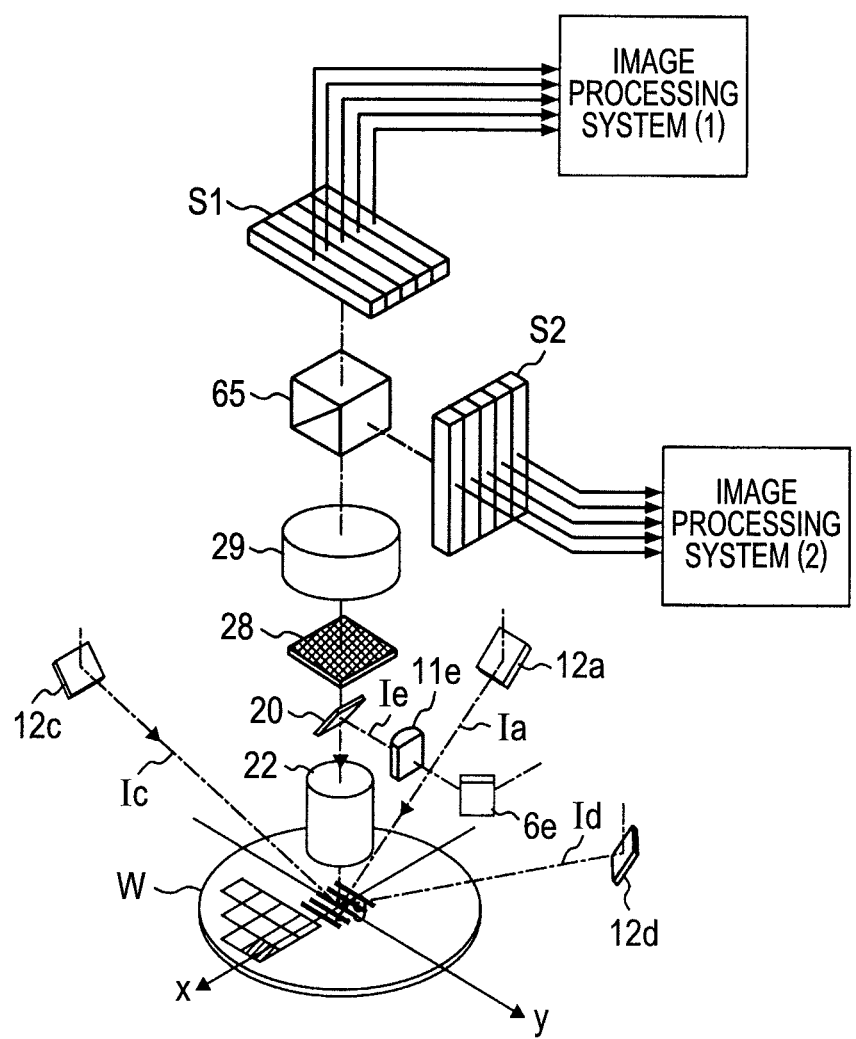
FIG. 40 is a diagram showing the detecting optical system according to Embodiment 4 of the present invention.

Next, Embodiment 4 of the present invention will be described with reference to FIGS. 39 and 40. Embodiment 4 is different from the first to third Embodiments in the following: as shown in FIG. 39, in the illumination optical system 200, a laser beam having a wavelength λ1 emitted from the light source 1a and the laser beam having a wavelength λ2 emitted from a light source 1b are matched by a dichroic prism 65 and two matched beams are used as the illumination light. And as shown in FIG. 40, in the detecting optical system 400, the light path is separated for each wavelength by the diachronic prism 65, which are detected by the detectors S1 and S2 respectively configured to include linear sensor array or area sensor array different from each other. According to Embodiment 4, it is possible to capture the image of different 2 wavelengths (that is, different optical conditions) and since the information quantity is further increased comparing to that of the first to third embodiments, it is expected that sensitivity and supplementary rate are further increased and the classification and sizing accuracy are improved.

Embodiment 5

Figure 41A:
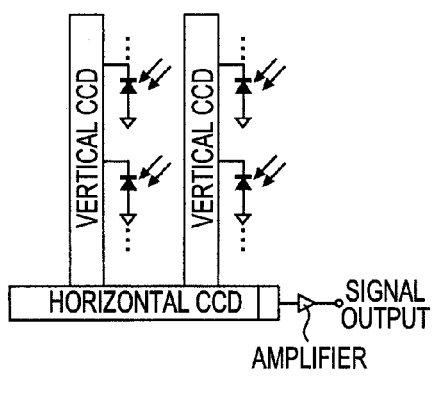
FIG. 41A is a diagram showing a configuration of a CCD sensor used as the detector that is common in the first to Embodiment 4s of the present invention and FIG. 41B is a diagram showing a configuration of a CMOS sensor used as the detector that is common in the first to Embodiment 4s of the present invention.
Figure 41B:
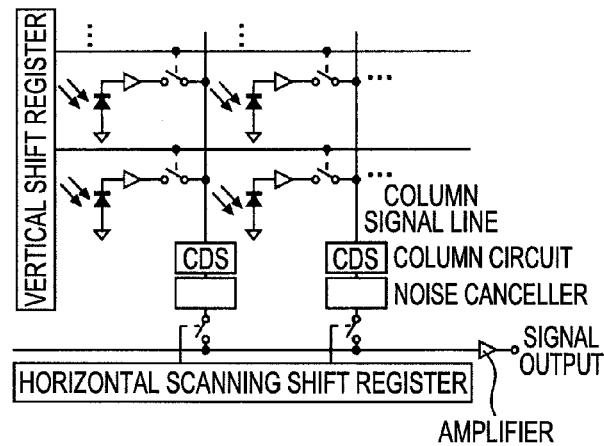

Next, the sensor commonly used in the Embodiments of the present invention will be individually described. Each linear sensor 30a to 30d or each area sensor 61a to 61d is roughly classified into a CCD sensor having a structure shown in FIG. 41(a) or a CMOS sensor shown in FIG. 41(b).

Figure 42A:
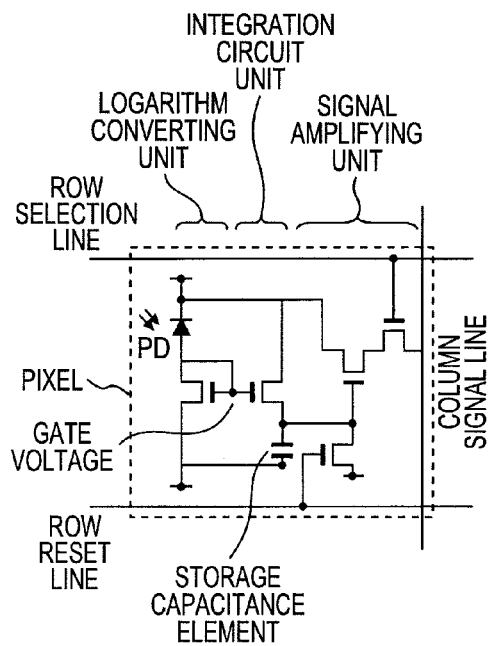
FIG. 42A is a diagram showing a state where each pixel of the CMOS sensor has a function of logarithmic conversion and FIG. 42B is a graph showing a state where incident light quantity dependence of a signal output of the CMOS sensor is represented by logarithmic characteristics.
Figure 42B:
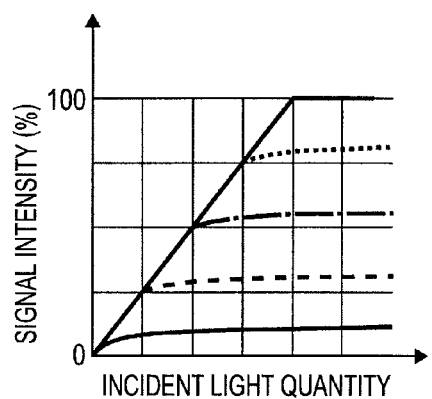
Figure 43A:
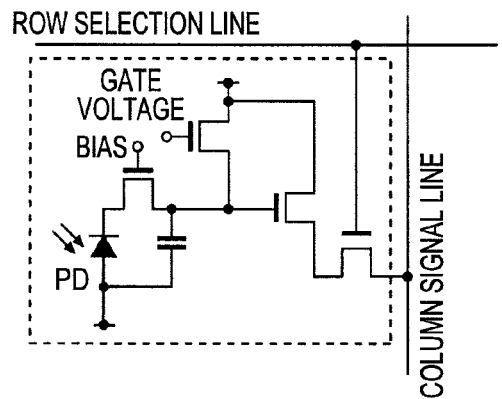
FIG. 43A is a diagram showing a circuit configuration for implementing a scheme called storage capacitance conversion.
Figure 43B:
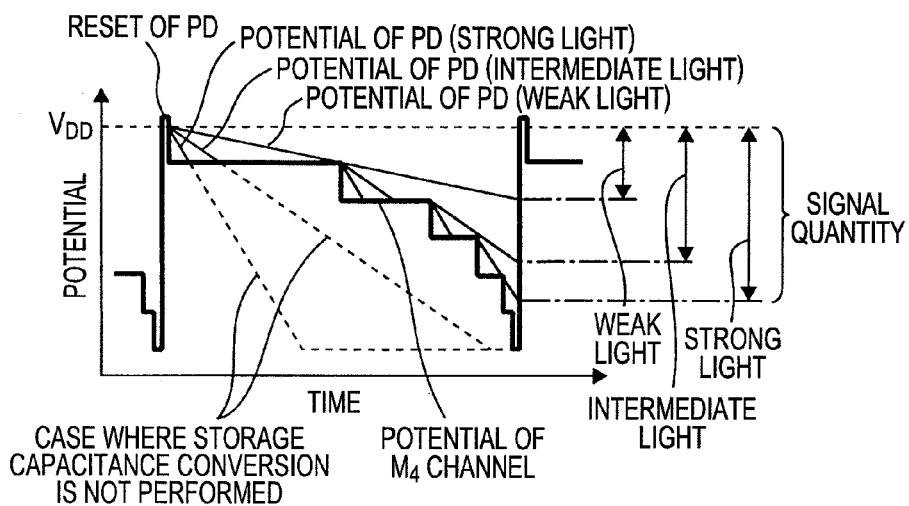
FIG. 43B is a graph showing a relationship between storage time and potential of a photodiode.
Figure 43C:
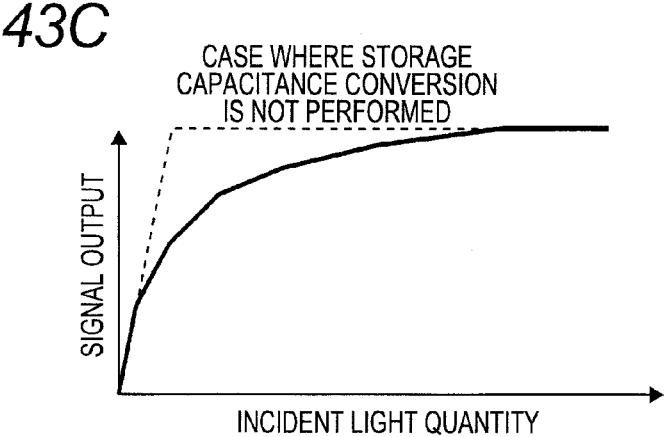
FIG. 43C is a graph showing a relationship between incident light quantity and sensor output.

Since the CMOS sensor has a circuit such as an amplifier for each pixel, it can implement the performance that is not implemented by the CCD sensor. For example, if each pixel has function of the logarithmic conversion shown in FIG. 42A, it is possible to make the incident light quantity dependence of the signal output as the logarithmic characteristics and pseudoly expanding the dynamic range of the sensor, as shown in FIG. 42B. Further, a circuit for implementing a scheme called the storage capacitance conversion is shown in FIG. 43A. It makes possible to change the potential of the photodiode (PD) according to strong light, intermediate light, and weak light by mounting the circuit on each of the pixels, as shown in FIG. 43B. As a result, as shown in FIG. 43C, even when the incident light quantity is strong, since light can be converted into electrical signals without saturating, it is possible to pseudoly expand the dynamic range of the sensor.

Figure 44A:
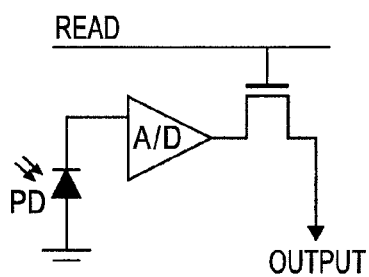
FIG. 44A is a diagram showing a circuit configuration for implementing a storage time control pseudoly expanding a dynamic range with the CMOS sensor used as the detector in the first to Embodiment 4s of the present invention and FIG. 44B is a diagram showing the incident light quantity dependence of a signal output.
Figure 44B:
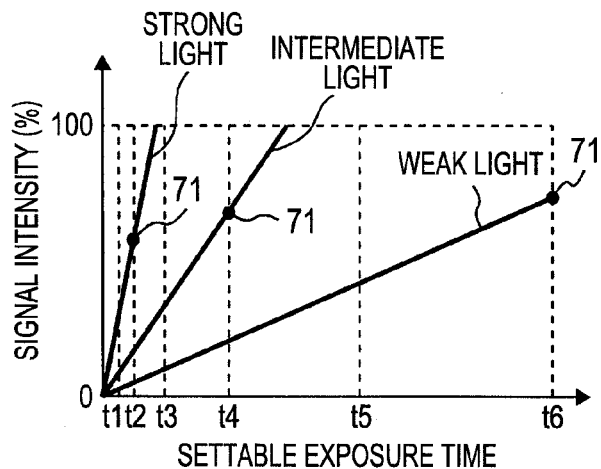
Figure 45:
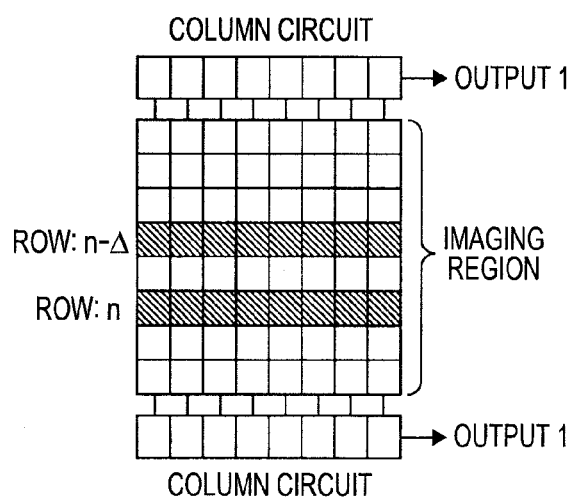
FIG. 45 is a diagram showing a circuit configuration for explaining a double sampling scheme pseudoly expanding a dynamic range with the CMOS sensor used as the detector in the first to Embodiment 4s of the present invention.
Figure 46A:
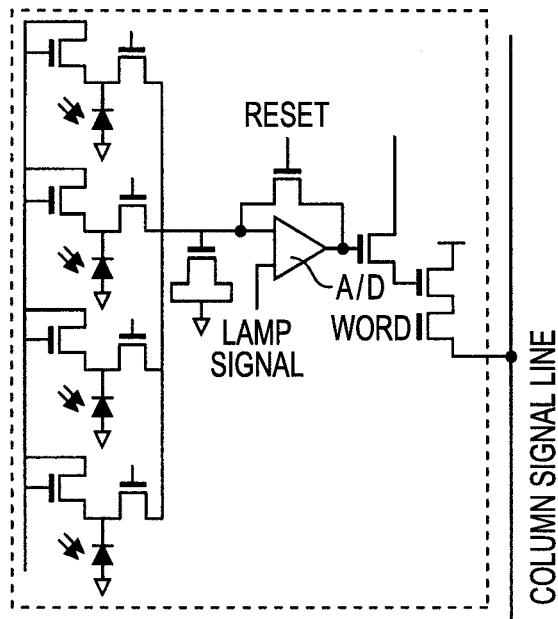
FIG. 46A is a diagram showing a pixel circuit having an in-pixel analog processing function in each pixel pseudoly expanding the dynamic range with the CMOS sensor used as the detector in the first to Embodiment 4s of the present invention and is a diagram showing a configuration in which one A-D converter shares four photodiodes and FIG. 46B is a diagram showing a pixel circuit having an in-pixel analog processing function in each pixel pseudoly expanding the dynamic range in the CMOS sensor.
Figure 46B:
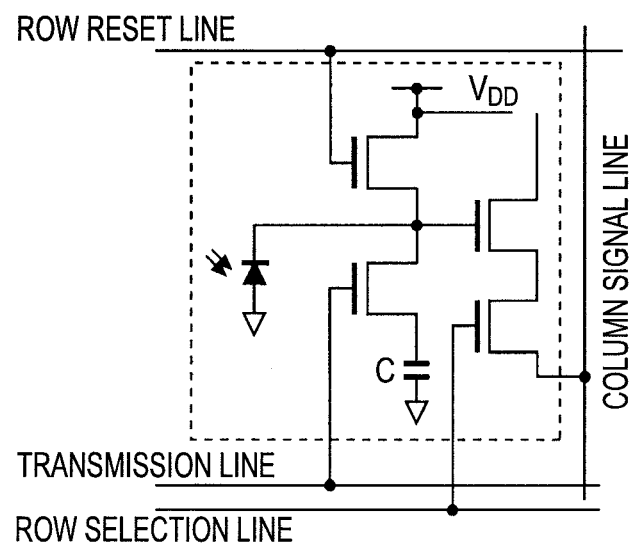

Further, there is a method of a wide dynamic range by a scheme of changing the exposure time (controlling the storage time) according to the incident strength shown in FIGS. 44A and 44B, or a dual sampling scheme shown in FIG. 45, or a scheme of sharing one A-D converter by four photodiodes shown in FIG. 46A, or a scheme having an analog processing function in a pixel shown in FIG. 46B. These technologies are described in detail in, for example, "Fundamentals and Applications of CCD/CMOS Image Sensor (CQ Publishing Co., Ltd.).

Figure 47:
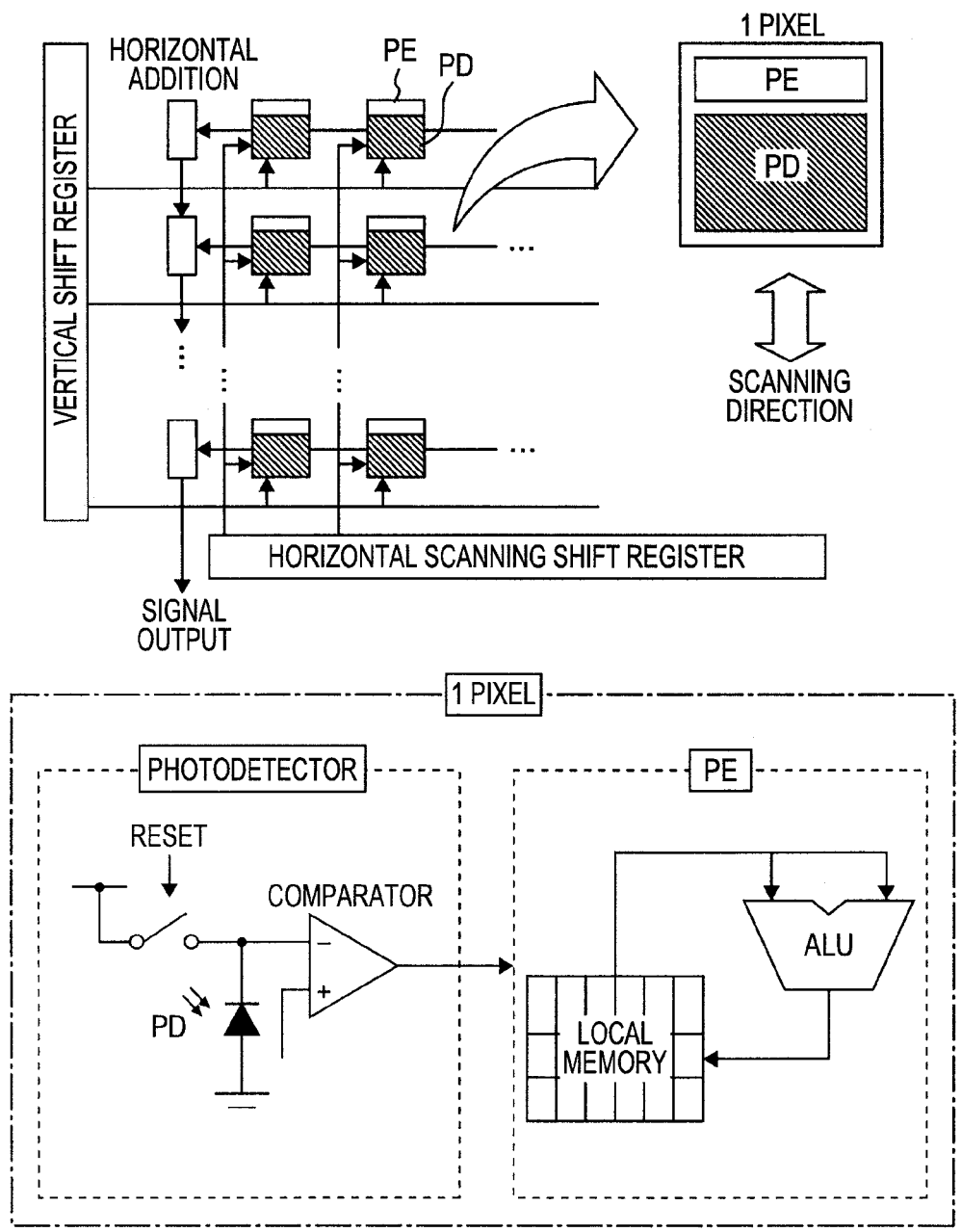
FIG. 47 is a diagram showing the CMOS sensor including a photodiode and a processor element (PE) in each pixel, which can be operational-processed with respect to each pixel and used as the detector in the first to Embodiment 4s of the present invention.

Further, as shown in FIG. 47, there is the CMOS sensor in which the processor element is mounted on the pixel. This has been known as a vision chip. The software A-D conversion, etc., that transmits the output from a comparator at the next stage of the photodiode to a processor element (PE), may be performed.

Figure 48:
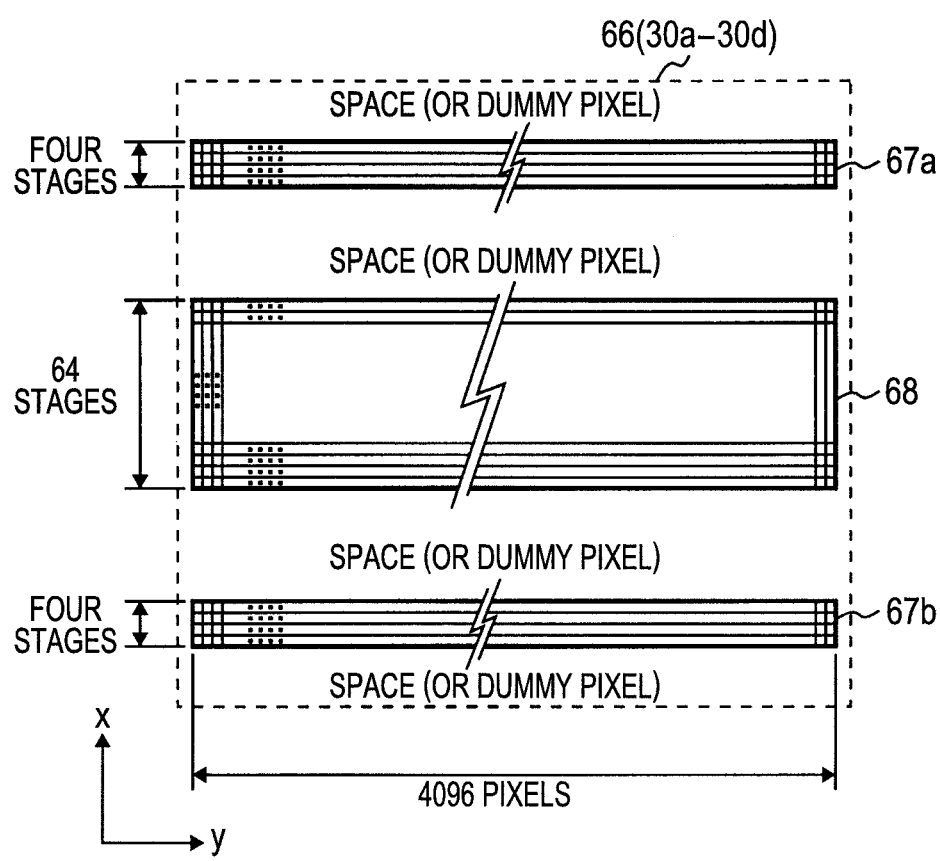
FIG. 48 is a diagram showing a fundamental element of the CMOS linear sensor having a light quantity monitor function and a soft TDI function used as the detector in the first to Embodiment 4s of the present invention.
Figure 49:
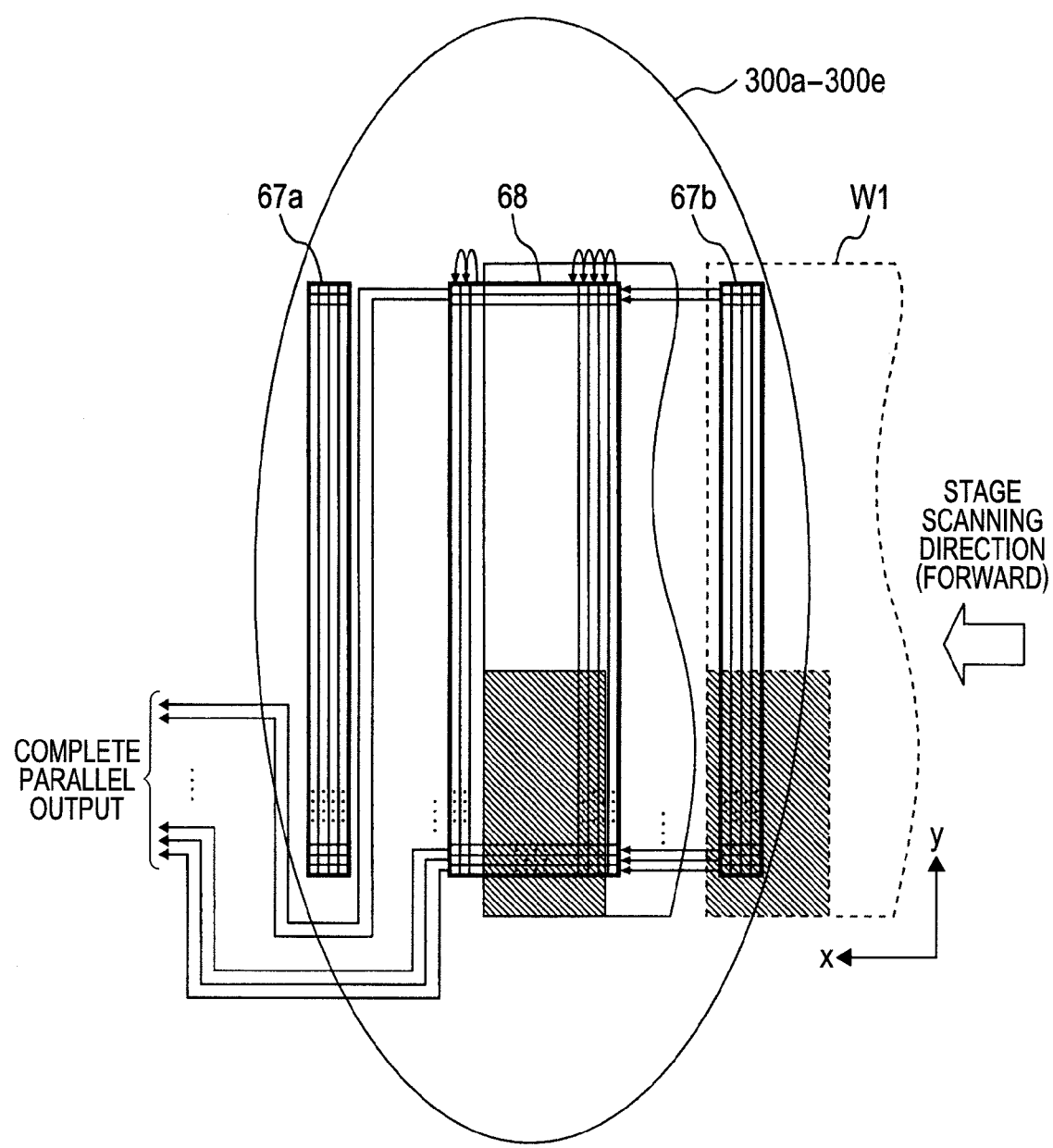
FIG. 49 is a diagram for explaining an operation of the CMOS linear sensor array having a light quantity monitor function and a soft TDI function used as the detector in the first to Embodiment 4s of the present invention.
Figure 50:
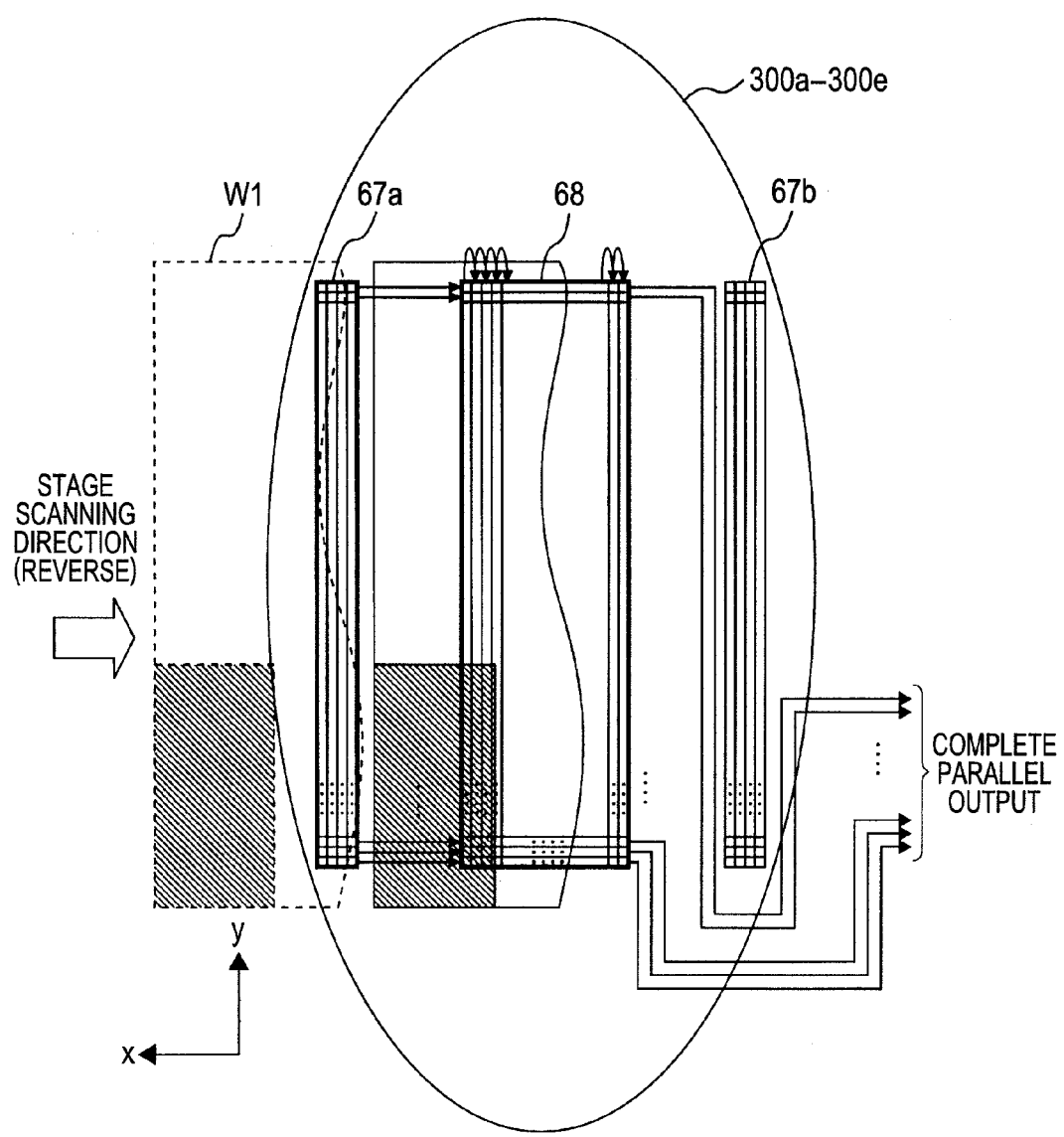
FIG. 50 is a diagram for explaining an operation of the CMOS linear sensor array having a light quantity monitor function and a soft TDI function used as the detector in the first to Embodiment 4s of the present invention.

FIGS. 48 to 52 show a linear sensor 66 (30a to 30d) using a CMOS sensor in which the PE is mounted on each pixel that can perform a high-performance flexible light quantity monitor, controlling the exposure time and the software TDI operation. In other words, each linear sensor 66 (30a to 30d) includes linear sensors 67a and 67b to which four-line PE is attached and a 64-line (64 stage) linear sensor 68. Next, the operation will be described with reference to FIGS. 49 and 50. As shown in FIG. 49, when a sample W1 having an area with different reflection rate is scanned from the right, the intensity of the reflected, diffracted, and scattered light is first measured by the linear sensor 67b to which the 4-line PE is attached. In other words, when it is set that each linear sensor can monitor light quantity for each column by using the 4-line linear sensor 67b, it is possible to monitor light quantity by 4 columns. By using the 4-line linear sensor, the information of the reflection rate of the sample measured by the 4-line linear sensor 67b is transmitted to the soft TDI unit 68 by inter-PE communication and by controlling the storage number of stages of the TDI unit 68 based on the information of the sample, it makes possible to receive light with the soft TDI unit without being saturated even for light signals in which the intensity from the sample having different reflection rate and having various signal intensities. Further, the exposure time (the storage number of stages of the soft TDI unit 68) is controlled and the detected signal without being saturated is completely output in parallel for each line from the final stage of the soft TDI unit 68. Meanwhile, as shown in FIG. 50, in the case where the scanning direction is in reverse, the intensity of the reflected, diffracted, and scattered light from the sample W is measured by the linear sensor 67a to which the 4-line PE is attached. In other words, when it is set that each linear sensor can monitor light quantity for each column by using the 4-line linear sensor 67a, it is possible to monitor light quantity for each 4 columns. By using the 4-line linear sensor, the information of the reflection rate of the sample measured by the 4-line linear sensor 67a is transmitted to the soft TDI unit 68 by inter-PE communication and by controlling the storage number of stages of the TDI unit 68 based on the information of the sample, it makes possible to receive light with the soft TDI unit without being saturated even for light signals in which the intensity from the sample having different reflection rate and having various signal intensities.

Figure 51A:
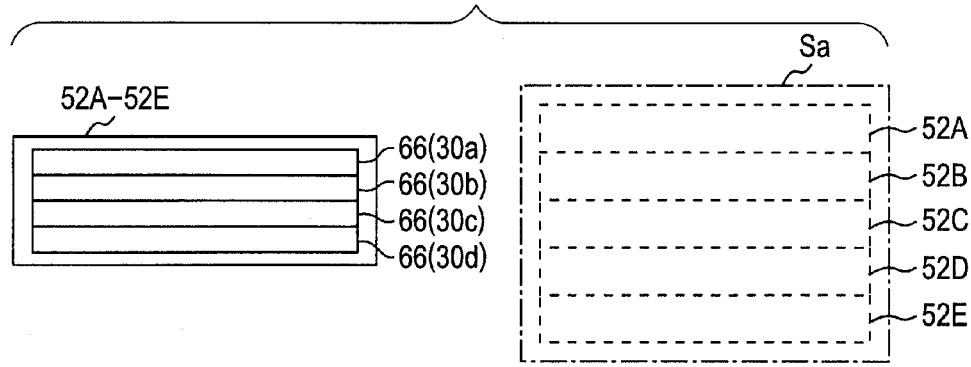
FIG. 51A shows a case where five linear sensor arrays having, for example, four image sensors disposed in a line are disposed in a line to be adjacent to each other, as a detector Sa that is the implementation form of the CMOS linear sensor array having a light quantity monitor function and a soft TDI function used as the detector in the first to Embodiment 4s of the present invention.
Figure 51B:
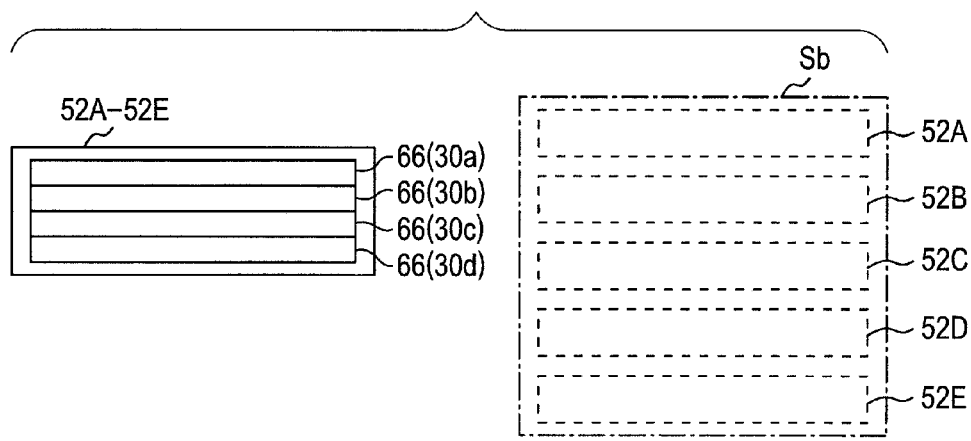
FIG. 51B shows a case where five linear sensor arrays having, for example, four image sensors disposed in a line are disposed in a line to be spaced apart from each other, as a detector Sb that is the implementation form of the CMOS linear sensor array having a light quantity monitor function and a soft TDI function.
Figure 51C:
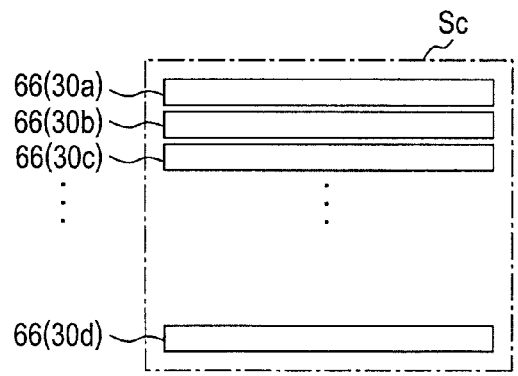
FIG. 51C shows a case where for example, twenty image sensors are configured to be simply disposed in a line, as a detector Sc that is the implementation form of the CMOS linear sensor array having a light quantity monitor function and a soft TDI function.
Figure 52:
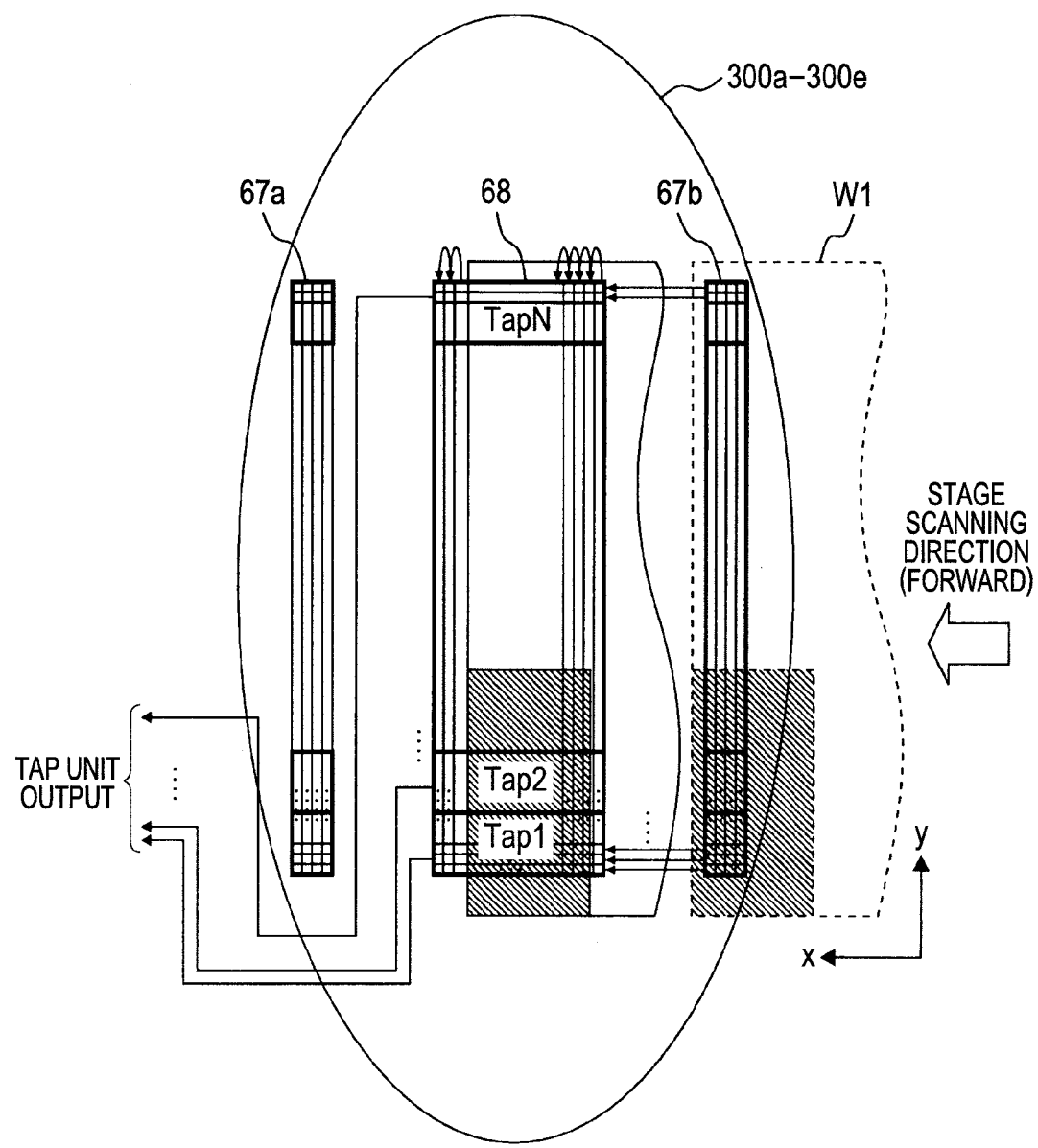
FIG. 52 is a diagram for explaining an operation of a case processing a signal in a tap unit in the CMOS linear sensor array having a light quantity monitor function and a soft TDI function used as the detector in the first to Embodiment 4 of the present invention.

In order to apply the above-mentioned each image sensor 66 (30a to 30d) to the embodiments of the present invention, as shown in FIG. 51, it is preferable that the component 66 shown in FIG. 48 is arranged in plural as 1 unit. FIG. 51A shows a case where five linear sensor arrays 52A to 52E in which, for example, four image sensors 66 (30a to 30d) are arranged are arranged to be adjacent to each other as the detector Sa, FIG. 51B shows a case where five linear sensor arrays 52A to 52E in which, for example, four image sensors 66 (30a to 30d) are arranged are arranged to have a gap as the detector Sb, and FIG. 51C shows a case where, for example, twenty image sensors 66 (30a to 30d) are simply arranged as the detector Sc. Further, as shown in FIG. 52, the signal processing in the 64-line (64 stages) linear sensor 68 may also be performed for each tap.

The present invention is not limited to the above-mentioned embodiments but may be practiced as being substituted into the same or equivalent one to operation described in the embodiment.

According to the embodiments of the present invention, it can be used as the foreign material and defect inspection device during the manufacturing of the semiconductor.

EXPLANATION OF REFERENCE NUMERALS AND SYMBOLS

1: Laser Light Source
2: Attenuator
3A to 3D: ½ Wavelength Plate
4A to 4D: ¼ Wavelength Plate
5:
6, 6A to 6D: Mirror
7A, 7B: Beam Splitter
8: Beam Expander
10A to 10D: Linear Polarizing Plate
11A to 11D: Cylindrical Lens
12A to 12D: Mirror For Adjusting Lighting Angle
13A to 13D: Linear Polarizing Plate
14A to 14D: Light Branching Element
20: Half Mirror
22: Objective Lens
23: X Stage
24: Y Stage
25: Rotation Stage
28: Spatial Filter
29: Imaging Lens
30A to 30D: One-Dimensional Linear Sensor
34: Subtraction Circuit
35: Memory
36: Threshold Value Processing Circuit
37: Comparison Circuit
38: Defect Determining Unit
39: Classification And Sizing Processing Unit
47A, 47B: Photonic Crystal
50: Feature Quantity Extracting Unit
52A to 52E: Linear Sensor Array
59: Light Shielding Plate
61A to 61D: Area Sensor
65: Dichloric Prism
100, 100A to 100E: Signal Processing Unit
101: Computer
103: External Device
104: Polarization Operational Processing Circuit
105: Merge Processing Circuit
200: Lighting Optical System
300A to 300E: Linear Beam
400: Detecting Optical System

The invention claimed is:

1. The defect inspection apparatus, comprising:
an illumination optical system configured to illuminate a specimen with a plurality of linear shaped beams;
an imaging optical system configured to generate an image resulting from light reflected and scattered from defects existing on the specimen, in response to illumination by the linear shaped beams from the illumination optical system;
a spatial filter disposed in the imaging optical system, and configured to shield diffracted light generated from a repetitive pattern formed on the specimen;
a detector configured to detect signals by receiving the light image generated by the imaging optical system and obtained through the spatial filter;
a defect determining unit configured to process the signals detected by the detector in order to determine defects on the specimen; and
a classification and sizing processing unit configured to classify defects determined in the defect determining unit, and configured to calculate a size of each defect,
wherein the illumination optical system illuminates the specimen with the plurality of linear shaped beams having different polarization components, to positions different from each other on the specimen, at almost the same time,
wherein the imaging optical system generates the plurality of images, of light reflected and scattered from the defects existing on the specimen, by the illumination of the plurality of linear shaped beams from the illumination optical system, and
wherein the detector includes linear sensor arrays, each of which is placed at a position where each of the plurality of images of reflected and scattered light has polarization components different from each other, and corresponding to the areas on the specimen illuminated by the plurality of linear shaped beams, and each of the linear sensor arrays receives an image different from others in polarization state.

2. The defect inspection apparatus according to claim 1, wherein in the detector, the plurality of polarization components different from each other include: −45°, 45°, 0°, and 90°.

3. The defect inspection apparatus according to claim 1, wherein the detector has a plurality of pixels of a linear polarization plate having a transmission axis different from each other, so as to receive the plurality of polarization components different from each other, at almost the same time, or individually.

4. The defect inspection apparatus according to claim 3, wherein the pixels of the linear polarization plate are formed of a photonic crystal.

5. The defect inspection apparatus according to claim 1, wherein the detector is configured of a CMOS type image sensor that can be processed in a pixel unit.

6. The defect inspection apparatus according to claim 1, wherein the CMOS type image sensor is configured so that characteristics of a sensor output to incident light quantity have logarithm characteristics.

7. The defect inspection apparatus according to claim 1, wherein the illumination optical system is configured to branch the beams emitted from the laser light source into a plurality of light paths, to adjust the polarization state in each of the branched light paths, and to illuminate the substrate with each of the linear shaped beams.

8. The defect inspection apparatus according to claim 1, wherein in the illumination optical system, the plurality of linear shaped beams are arranged to illuminate a plurality of positions on the specimen which are different from each other, at almost the same time, so that the longitudinal direction of the plurality of linear shaped beams that illuminate the specimen are approximately at a right angle to a travelling direction of a stage which mounts the specimen.

9. A defect inspection apparatus, comprising:
an illumination optical system configured to illuminate a specimen with a plurality of linear shaped beams, at almost the same time, wherein the plurality of linear shaped beams differ from each other in terms of polarization components, and in terms of positions on the specimen;
an imaging optical system configured to generate an image resulting from light reflected and scattered from defects existing on the specimen, in response to illumination by the plurality of linear shaped beams from the illumination optical system, and;
a spatial filter disposed in the imaging optical system, and configured to shield diffracted light generated from a repetitive pattern formed on the specimen;
a detector configured to detect signals by receiving a light image generated by the imaging optical system and obtained through the spatial filter;
a defect determining unit configured to process the signals detected by the detector in order to determine defects on the specimen; and
a classification and sizing processing unit configured to classify defects determined in the defect determining unit and configured to calculate a size of each defect,
wherein the detector includes a plurality of linear sensor arrays, each of which includes a CMOS type image sensor having plural pixel units that can process the detected signals in each of the pixel units, and placed at a position where each of the plurality of images resulting from light reflected and scattered from defects have a plurality of polarization components different from each other,
wherein the images correspond to the areas on the specimen illuminated by the plurality of linear shaped beams, and
wherein each of the linear sensor arrays receives an image different from the others in polarization state.

10. The defect inspection apparatus of claim 9, wherein the CMOS type image sensor has a logarithmic output characteristic in relation to incident light quantity.

11. A defect inspection method, comprising the steps of:
illuminating a plurality of linear shaped beams from an illumination optical system, the beams having different polarization components, onto positions different from each other on a specimen, at almost the same time;
generating images, resulting from light reflected and scattered from defects existing on the specimen, the light being originally the linear shaped beams from the illumination optical system;
using a a spatial filter to shield diffracted light generated from a repetitive pattern formed on the specimen;
receiving images by a detector, said image being obtained through the spatial filter and imaged on a detector at the imaging step, the detector including a plurality of linear sensor arrays, each of which is placed at a position where each of the plurality of light images have a plurality of polarization components different from each other, and the images correspond to the areas on the specimen illuminated by the plurality of linear shaped beams;
detecting signals by use of the detector;
processing the signals detected by the detector during the detecting step, and determining defects on the specimen; and
classifying the defects determined during the defect determining step and calculating the size of the defects.

12. The defect inspection method according to claim 11, wherein in the illuminating step, the illumination optical system illuminates a plurality of positions on the specimen, which are different from each other, with a plurality of linear shaped beams, at almost the same time,
wherein in the imaging step, the imaging optical system generates the plurality of reflected and scattered light images reflected from the defects existing on the specimen, by the irradiation of the plurality of linear shaped beams during the illuminating step, and
wherein in the receiving a light image step, the detector receives the plurality of light images imaged in the imaging step at almost the same time, or individually, to detect the plurality of signals.

13. The defect inspection method according to claim 12, wherein in the illuminating step, the plurality of linear shaped beams are arranged to illuminate a plurality of positions on the specimen which are different from each other, at almost the same time, so that the longitudinal direction of the plurality of linear beams illuminating the specimen are at an approximately right angle to a travelling direction of a stage which mounts the specimen.

14. The defect inspection method according to claim 11, wherein in the detecting step, the detector has a plurality of pixels of the linear polarization plates having transmission axis different from each other, and the detector has a plurality of pixels of a linear polarizing plate having transmission axis different from each other receiving the plurality of polarization components different from each other, at almost the same time, or individually.

15. The defect inspection method according to claim 11, wherein in the illuminating step, the beams emitted from the laser light source are branched into a plurality of light paths, and the polarization state is adjusted in each of the branched light paths to illuminate the substrate with each of the linear shaped beams.

* * * * *